US008227437B2

(12) United States Patent
Yoo

(10) Patent No.: US 8,227,437 B2
(45) Date of Patent: Jul. 24, 2012

(54) RESTORATION OF HEARING LOSS

(76) Inventor: Tai June Yoo, Memphis, TN (US)

( * ) Notice: Subject to any disclaimer, the term of this patent is extended or adjusted under 35 U.S.C. 154(b) by 152 days.

(21) Appl. No.: 12/305,637

(22) PCT Filed: Jun. 19, 2007

(86) PCT No.: PCT/US2007/014391
§ 371 (c)(1),
(2), (4) Date: Apr. 29, 2010

(87) PCT Pub. No.: WO2007/149493
PCT Pub. Date: Dec. 27, 2007

(65) Prior Publication Data
US 2011/0086002 A1    Apr. 14, 2011

Related U.S. Application Data

(60) Provisional application No. 60/815,981, filed on Jun. 22, 2006.

(51) Int. Cl.
*A61K 48/00* (2006.01)
(52) U.S. Cl. .................................................. 514/44 R
(58) Field of Classification Search ................. 514/44 R
See application file for complete search history.

(56) References Cited

U.S. PATENT DOCUMENTS

| | | | |
|---|---|---|---|
| 5,437,994 | A | 8/1995 | Emerson et al. |
| 5,580,859 | A | 12/1996 | Felgner et al. |
| 5,589,466 | A | 12/1996 | Felgner et al. |
| 5,646,043 | A | 7/1997 | Emerson et al. |
| 5,670,147 | A | 9/1997 | Emerson et al. |
| 5,670,351 | A | 9/1997 | Emerson et al. |
| 5,676,954 | A | 10/1997 | Brigham |
| 5,693,622 | A | 12/1997 | Wolff et al. |
| 5,703,055 | A | 12/1997 | Felgner et al. |
| 5,763,270 | A | 6/1998 | Eastman et al. |
| 5,935,565 | A | 8/1999 | Besmer et al. |
| 6,034,072 | A | 3/2000 | Ralston et al. |
| 6,040,295 | A | 3/2000 | Rolland et al. |
| 6,080,728 | A | 6/2000 | Mixon |
| 6,093,531 | A | 7/2000 | Bjornson et al. |
| 6,261,549 | B1 | 7/2001 | Fernández et al. |
| 6,326,198 | B1 | 12/2001 | Emerson et al. |
| 6,413,955 | B1 | 7/2002 | Askew et al. |
| 6,506,559 | B1 | 1/2003 | Fire et al. |
| 6,710,035 | B2 | 3/2004 | Felgner et al. |
| 6,734,014 | B1 | 5/2004 | Hwu et al. |
| 6,875,748 | B2 | 4/2005 | Manthorpe et al. |
| 2001/0004456 | A1* | 6/2001 | Tobinick ............ 424/85.1 |
| 2001/0036644 | A1 | 11/2001 | Yoo |
| 2002/0019043 | A1* | 2/2002 | Steidler et al. ........ 435/252.3 |
| 2003/0203482 | A1* | 10/2003 | Kil et al. ............ 435/325 |
| 2006/0217332 | A1 | 9/2006 | Vargeese et al. |
| 2007/0020352 | A1* | 1/2007 | Tripp et al. ............ 424/778 |

FOREIGN PATENT DOCUMENTS

| | | |
|---|---|---|
| WO | WO 90/11092 | 10/1990 |
| WO | WO 94/24983 | 11/1994 |
| WO | WO 94/29469 | 12/1994 |
| WO | WO03/045318 A2 * | 6/2003 |

OTHER PUBLICATIONS

Acsadi et al., Human dystrophin expression in mdx mice after intramuscular injection of DNA constructs, Nature 352: 815-818 (1991).
Anderson, W.F., Human Gene Therapy, Science 256(5058):808-13 (1992).
Araki, N., et al., Nematolysosomes (Elongate Lysosomes) in Rat Hepatocytes: Their Distribution, Microtubule Dependence, and Role in Endocytic Transport Pathway, Experimental Cell Research, vol. 204(2), p. 181-91 (1993).
Berge et al., Pharmaceutical Salts, Journal of Pharmaceutical Sciences 66:1-19 (1977).
Brown and Goldstein, A Receptor-Mediated Pathway for Cholesterol Homeostasis, Science 232:34-47 (1986).
Bulinski, J.C., et al., Stabilization of post-translational modification of microtubules during cellular morphogenesis, Bio. Essays, vol. 13,(1991).
Caplen et al., Lipisome-mediated *CFTR* gene transfer to the nasal epithelium of patients with cystic fibrosis, Nature Med., 1:39-46 (1995).
Chen et al., Co-polymer of histidine and lysine markedly enhances transfection efficiency of liposomes, Gene Therapy 7(19):1698-705 (2000).
Cheng, K.C., et al., Proto-oncogene Raf-1 as an Autoantigen in Meniere's Disease, Annal. Otol. Rhinol. Laryngol., vol. 109 (12 Pt. 1), p. 1093-98 (1997).
Connolly, A.M., et al., Serum IgM monoclonal autoantibody binding to the 301 to 314 amino acid epitope of β-tubulin: Clinical association with slowly progressive demyelinating polyneuropathy, Neurology, vol. 48, p. 243-48 (1997).
Costa et al., Targeting Rare Populations of Murine Antigen-Specific T Lymphocytes by Retroviral Transduction for Potential Application in Gene Therapy for Autoimmune Disease, J. Immunol., 164:3581-90 (2000).
Costa et al., Adoptive Immunotherapy of Experimental Autoimmune Encephalomyelitis Via T Cell Delivery of the IL-12 p40 Subunit, J. Immunol., vol. 167(4), p. 2379-87 (2001).
Curiel et al., High-Efficiency Gene Transfer Mediated by Adenovirus Coupled to DNA-Polylysine Complexes, Human Gene Therapy, 3:147-154 (1992).
Davis et al., Direct Gene Transfer into Skeletal Muscle In Vivo: Factors Affecting Efficiency of Transfer and Stability of Expression, Human Gene Therapy 4:151-159 (1993).

(Continued)

*Primary Examiner* — Brian Whiteman
(74) *Attorney, Agent, or Firm* — Foley & Lardner LLP

(57) ABSTRACT

The present invention relates to compositions and methods for restoring hearing loss. In particular aspects, the invention relates to the administration of compositions that encode an inflammatory response control element. The compositions are prepared and administered in such a manner that the inflammatory response control element coding sequence is expressed in the subject to which the composition is administered. The compositions include expression systems, delivery systems, and certain inflammatory response control genes.

10 Claims, 10 Drawing Sheets

OTHER PUBLICATIONS

Deanin, G.G., et al., Carboxyl Terminal Tyrosine Metabolism of Alpha Tubulin and Changes in Cell Shape: Chinese Hamster Ovary Cells, Biochem. Biophys. Res. Commun., vol. 1, p. 1642-50 (1981).

Donnelly et al., Immunization with DNA, J Immunol Meth. 176:145-152 (1994).

Dzau et al., Gene therapy for cardiovascular disease, Trends in Biotechnology 11(5):205-10 (1993).

Eck et al., Gene-based Therapy, in Goodman & Gilman's The Pharmacological Basis of Therapeutics, Ninth Edition, Hardman et al., eds., McGray-Hill, New York, Chapter 5, pp. 77-101, (1996).

Felgner et al., Lipofection: A highly efficient, lipid-mediated DNA-transfection procedure, Proc. Natl. Acad. Sci. 84: 7413-7417 (1993).

Garcia, G. et al., Suppression of Collagen-induced Arthritis by Oral or Nasal Administration of Type II Collagen, J Autoimmunity, vol. 13, p. 315-24 (1999).

Gunderson, G.G., et al., Postpolymerization Detyrosination of α-Tubulin: A Mechanism for Subcellular Differentiation of Microtubules, J. Cell Biol., vol. 105, p. 251-64 (1987).

Harrison, L.C., Hafler, D.A., Antigen-specific therapy for autoimmune disease, Current Opinion in Immunology, vol. 12(2), p. 704-11 (2000).

Horsfall, A.C., et al., Suppression of Collagen-Induced Arthritis by Continuous Administration of IL-4, J Immunol., vol. 159, p. 5687-96 (1997).

Hyde, G.J., et al., Microtubules regulate the generation of polarity in zoospores of Phytophthora cinnamomi, Eur. J. Cell Biol., vol. 62, abstract only (1993).

Inobe, J., et al., IL-4 is a differentiation factor for transforming growth factor-β secreting Th3 cells and oral administration of IL-4 enhances oral tolerance in experimental allergic encephalomyelitis, Eur. J. Immunol., vol. 28, p. 278-79 (1998).

Kaneda et al., Increased expression of DNA cointroduced with nuclear protein in adult rat liver, Science 243.abstract only (1989).

Kim et al., Effective Treatment of Established Murine Collagen-Induced Arthritis by Systemic Administration of Dendritic Cells Genetically Modified to Express IL-4, J. Immunol. 166(21):3499-3550 (2001).

Kurisaki, H., et al., [Immunocytochemical study of spheroid filament protein in amyotrophic lateral sclerosis using an antiserum to 200K peptide of neurofilament and anti-tubulin antibody] J. Rinsho-shin Keigakee Clin. Neuro., vol. 23, (1983).

Leach, M.W., et al., Safety Evaluation of Recombinant Human Interleukin-4, I. Preclinical Studies, Clin. Immunol. Immunopathol., vol. 83, p. 8-11 (1997).

Lesoon-Wood et al., Systemic Gene Therapy with p53 Reduces Growth and Metastases of a Malignant Human Breast Cancer in Nude Mice, Human Gene Therapy 6:395-405 (1995).

Ling, P., et al., Human IL-12 p40 Homodimer Binds to the IL-12 Receptor but Does Not Mediate Biologic activity, J. Immunol., vol. 154, p. 116-27 (1995).

Manfredini, E., et al., Anti-alpha- and beta-tubulin IgM antibodies in dysimmune neuropathies, J. Neuro. Sci., vol. 133, p. 79-84 (1995).

Mannino et al., Lipisome mediated gene transfer, Biotechniques 6, abstract only (1988).

Matsuoka, H., Cheng, K.C., et al., Murine Model of Autoimmune Hearing Loss Induced by Myelin Protein P0, Annals Oto. Rhino. Laryngol., vol. 108 (3), p. 255-64 (1998).

Mettner, F., et al., The interleukin-12 subunit p40 specifically inhibits effects of the interleukin-12 heterodimer, Eur. J. Immunol., vol. 23, (1993), abstract only.

Morita et al., Dendritic cells genetically engineered to express IL-4 inhibit murine collagen-induced arthritis, J. Clin. Invest., 17(21):1275-84 (2001).

Nakajima, A., Seroogy, C.M., et al., Antigen-specific T cell-mediated gene therapy in collagen-induced arthritis, J. Clin. Invest., vol. 107, p. 1293-1301 (2001).

Nicolau et al., In vivo expression of rat insulin after intravenous administration of the lipisome-entrapped gene for rat insulin I, Proc. Natl. Acad. Sci USA 80:1068-1072 (1983).

Rabinovich et al., Recombinant Galectin-1 and its Genetic Delivery Suppress Collagen-Induced Arthritis via T Cell Apoptosis J. Exp. Med., 19:385-98 (1999).

Racke, M.K., et al., Cytokine-induced Immune Deviation as a Therapy for Inflammatory Autoimmune Disease, J. Exp. Med., vol. 18, p. 1961-66 (1994).

Raz et al., Intradermal gene immunization: The possible role of DNA uptake in the induction of cellular immunity to viruses, Pro. Natl. Acad. Sci. 91:9519-9523 (1994).

Recombinant DNA Advisory Committee Data Management Report, Human Gene Therapy 6: 535-548 (1994).

Romano et al., Latest Developments in Gene Transfer Technology: Achievements, Perspectives, and Controversies over Therapeutic Applications, Stem Cells, 18:19-39 (2000).

Rosenberg et al., Grafting Genetically Modified Cells to the Damaged Brain: Restorative Effects of NGF Expression, Science, 242:1575-1578 (1988).

Rousset et al., Anti-tubulin antibodies in autoimmune thyroid disorders, Clin. Exp. Immunol., vol. 52, p. 325-32 (1984).

Rousset et al., Anti-tubulin antibodies in recent onset Type 1 (insulin-dependent) diabetes mellitus: comparison with islet cell antibodies, Diabetologia 27:427-432 (1984).

Sato et al., Immunostimulatory DNA Sequences Necessary for Effective Intradermal Gene Immunization, Science 273: 352-354 (1996).

Schulze, E., et al., Dynamic and Stable Populations of Microtubules in Cells, J. Cell Biol., vol. 104, p. 277-88 (1987).

Segal, B.M., et al., An Interleukin (IL)-10/IL-12 Immunoregulatory Circuit Controls Susceptibility to Autoimmune Disease, J. Exp. Med., vol. 187, p. 537-46 (1998).

Seroogy et al., The application of gene therapy in autoimmune diseases, Gene Therapy, 7:9-13 (2000).

Tang et al. Genetic immunization is a simple method for eliciting an immune response, Nature 356:152-154, (1992).

Tannenbaum, J., et al., Localization of Microtubules Containing Posttranslationally Modified Tubulin in Cochlear Epithelial Cells During Development, vol. 38, p. 146-162 (1997).

Tarner, I.H., et al., Gene therapy in autoimmune disease, Curr. Opinion Immunol., vol. 13 (21), p. 676-82 (2001).

Tominaga, Y., et al., Administration of IL-4 Prevents Autoimmune Diabetes but Enhances Pancreatic Insulitis in NOD Mice, Clin. Imnnol. Immunopathol., vol. 86, p. 209-18 (1998).

Tuohy et al., T cell design for therapy in autoimmune demyelinating disease, J. Neuroimmunol., 17(2):226-32 (2000).

Wagner et al., Transferring-polycation conjugates as carriers for DNA uptake into cells. Proc. Natl. Acad. Sci. USA 87(9):3410-4 (1990).

Wilson, J.M., Vectors—shuttle vehicles for gene therapy. Clin. Exp. Immunol. 107 (Suppl. 1):31-32 (1997).

Wivel N.A., MD and Wilson, J.M., MD, PhD, Methods of Gene Delivery, Hematology/Oncology Clinics of North America, Gene Therapy, S.L. Eck, ed., 12(3):483-501 (1998).

Wolff et al., Grafting fibroblasts genetically modified to produce L-dopa in a rat model of Parkinson disease, Proc. Natl. Acad. Sci. USA 86:9011-9014 (1989).

Wolff et al., Direct gene transfer into mouse muscle in vivo. Science, 247, abstract only (1990).

Wolff et al., Long-term persistence of plasmid DNA and foreign gone expression in mouse muscle. Hum. Mol. Genet. 1:363-69 (1992).

Wu, G.Y. and Wu, C.H., Receptor-mediated in Vitro Gene Transformation by a Soluble DNA Carrier System. J. Biol. Chem. 262(10):4429-32 (1987).

Xu et al., Gene Therapy with P53 and a Fragment of Thrombospondin I Inhibits Human Breast Cancer in Vivo, Molecular Genetics and Metabolism, 63:103-109 (1998).

Yoo, T.J., Stuart, J.M., et al., Type II Collagen Autoimmunity in Otosclerosis and Meniere's Disease, Science, vol. 217:1153-55 (1982).

Yoo, T.J., Tanaka, H., et al., β-Tubulin as an Autoantigen for Autoimmune Inner Ear Disease, Meniere's Disease update, p. 529-535 (1999).

Yoo, T.J., Tomoda, K., et al., Type II Collagen-Induced Autoimmune Inner Ear Lesions in Guinea Pigs, Annal. Otol. Rhinol. Laryngol., vol. 93 (suppl. 113), p. 3-5.(1984).

Yoo, T. and Yazawa, Y., Immunology of cochlear and vestibular disorders, Fundamentals of audiological and vestibular medicine, Textbook of Audiological Medicine, Clinical Aspects of Hearing and Balance, Chapter 5, pp. 61-87 (2003).

Zhu et al., Systemic gene expression after intravenous DNA delilvery into adult mice, Science, 261:abstract only (1993).

Xu et al., A Role for c-Raf kinase and Ha-Ras in cytokine-mediated induction of Cell adhesion molecules. The Journal of Biological Chemistry, 273(50): p. 33230-33238, 1998.

International Search Report for PCT Patent Application No. PCT/US2007/014391 dated Sep. 9, 2008.

* cited by examiner

CB 11 peptide of type II collagen DNA Sequence Range: 5910 to 6806

>Start_of_bCB11_coding_sequence.
>bCB11_insert
>Bgl_II_Site

```
5910         5920         5930         5940    |    5950         5960
  *            *            *            *            *            *
TAC GAC GAT GAC GAT AAG GAT CCG AGC TCG AGA TCT ATG GGT CCT CGT GGC CTG
ATG CTG CTA CTG CTA TTC CTA GGC TCG AGC TCT AGA TAC CCA GGA GCA CCG GAC
 Y   D   D   D   D   K   D   P   S   S   R   S   M   G   P   R   G   L 5970         5980         5990         6000         6010
          *            *            *            *            *
CCT GGT GAA AGA GGA CGG ACT GGC CCT GCC GGC GCT GCA GGT GCT CGA GGC AAT
GGA CCA CTT TCT CCT GCC TGA CCG GGA CGG CCG CGA CGT CCA CGA GCT CCG TTA
 P   G   E   R   G   R   T   G   P   A   G   A   A   G   A   R   G   N 6020         6030         6040         6050         6060         6070
  *            *            *            *            *            *
GAC GGT CAG CCA GGC CCT GCA GGG CCT CCG GGT CCT GTG GGT CCT GCT GGC GGT
CTG CCA GTC GGT CCG GGA CGT CCC GGA GGC CCA GGA CAC CCA GGA CGA CCG CCA
 D   G   Q   P   G   P   A   G   P   P   G   P   V   G   P   A   G   G 6080         6090         6100         6110         6120
          *            *            *            *            *
CCT GGC TTT CCT GGT GCT CCT GGT GCC AAG GGT GAA GCT GGC CCC ACC GGT GCT
GGA CCG AAA GGA CCA CGA GGA CCA CGG TTC CCA CTT CGA CCG GGG TGG CCA CGA
 P   G   F   P   G   A   P   G   A   K   G   E   A   G   P   T   G   A 6130         6140         6150         6160         6170
          *            *            *            *            *
CGA GGT CCC GAA GGC GCC CAG GGT CCT CGC GGT GAA CCG GGT ACT CCT GGG TCC
GCT CCA GGG CTT CCG CGG GTC CCA GGA GCG CCA CTT GGC CCA TGA GGA CCC AGG
 R   G   P   E   G   A   Q   G   P   R   G   E   P   G   T   P   G   S 6180         6190         6200         6210         6220         6230
  *            *            *            *            *            *
CCT GGG CCA GCT GGT GCT GCT GGC AAC CCT GGA ACT GAT GGA ATC CCT GGA GCC
GGA CCC GGT CGA CCA CGA CGA CCG TTG GGA CCT TGA CTA CCT TAG GGA CCT CGG
 P   G   P   A   G   A   A   G   N   P   G   T   D   G   I   P   G   A 6240         6250         6260         6270         6280
          *            *            *            *            *
AAG GGA TCT GCT GGT GCC CCT GGC ATT GCT GGT GCT CCC GGC TTC CCT GGA CCC
TTC CCT AGA CGA CCA CGG GGA CCG TAA CGA CCA CGA GGG CCG AAG GGA CCT GGG
 K   G   S   A   G   A   P   G   I   A   G   A   P   G   F   P   G   P 6290         6300         6310         6320         6330         6340
  *            *            *            *            *            *
CGT GGT CCA CCC GGC CCT CAA GGT GCA ACT GGT CCT CTG GGC CCA AAA GGT CAA
GCA CCA GGT GGG CCG GGA GTT CCA CGT TGA CCA GGA GAC CCG GGT TTT CCA GTT
 R   G   P   P   G   P   Q   G   A   T   G   P   L   G   P   K   G   Q
```

Figure 11

```
              6350            6360            6370            6380            6390
               *               *               *               *               *
       ACG GGT GAG CCT GGT ATT GCT GGC TTC AAA GGC GAA CAA GGC CCC AAG GGA GAA
       TGC CCA CTC GGA CCA TAA CGA CCG AAG TTT CCG CTT GTT CCG GGG TTC CCT CTT
        T   G   E   P   G   I   A   G   F   K   G   E   Q   G   P   K   G   E 6400            6410            6420            6430            6440
           *               *               *               *               *
       CCG GGC CCT ACT GGT CCC CAA GGA GCC CCT GGT CCT GCT GGT GAA GAA GGG AAA
       GGC CCG GGA TGA CCA GGG GTT CCT CGG GGA CCA GGA CGA CCA CTT CTT CCC TTT
        P   G   P   T   G   P   Q   G   A   P   G   P   A   G   E   E   G   K 6450            6460            6470            6480            6490            6500
   *               *               *               *               *               *
AGA GGT GCC CGT GGA GAA CCT GGT GGT GCT GGG CCC GCC GGT CCC CCT GGA GAA
TCT CCA CGG GCA CCT CTT GGA CCA CCA CGA CCC GGG CGG CCA GGG GGA CCT CTT
 R   G   A   R   G   E   P   G   G   A   G   P   A   G   P   P   G   E 6510            6520            6530            6540            6550
           *               *               *               *               *
       AGA GGC GCT CCT GGA AAC CGT GGT TTC TCA GGT CAG GAT GGT CTG GCA GGT CCC
       TCT CCG CGA GGA CCT TTG GCA CCA AAG AGT CCA GTC CTA CCA GAC CGT CCA GGG
        R   G   A   P   G   N   R   G   F   S   G   Q   D   G   L   A   G   P 6560            6570            6580            6590            6600            6610
   *               *               *               *               *               *
AAG GGA GCC CCT GGA GAG CGA GGA CCC AGT GGC CTC GCT GGT CCC AAA GGC GCC
TTC CCT CGG GGA CCT CTC GCT CCT GGG TCA CCG GAG CGA CCA GGG TTT CCG CGG
 K   G   A   P   G   E   R   G   P   S   G   L   A   G   P   K   G   A 6620            6630            6640            6650            6660
               *               *               *               *               *
       AAC GGT GAC CCT GGC CGT CCC GGA GAG CCT GGC CTT CCT GGA AGC CCG GGT CTC
       TTG CCA CTG GGA CCG GCA GGG CCT CTC GGA CCG GAA GGA CCT TCG GGC CCA GAG
        N   G   D   P   G   R   P   G   E   P   G   L   P   G   S   P   G   L 6670            6680            6690            6700            6710
           *               *               *               *               *
       ACT GGT CGC CCT GGT GAT GCT GGT CCT CAA GGC AAA GTT GGT CCT TCC GGA GCC
       TGA CCA GCG GGA CCA CTA CGA CCA GGA GTT CCG TTT CAA CCA GGA AGG CCT CGG
        T   G   R   P   G   D   A   G   P   Q   G   K   V   G   P   S   G   A 6720           6730            6740            6750            6760            6770
   *              *               *               *               *               *
CCT GGT GAA GAC GGT CGC CCT GGA CCC CCA GGT CCT CAG GGG GCT CGT GGG CAG
GGA CCA CTT CTG CCA GCG GGA CCT GGG GGT CCA GGA GTC CCC CGA GCA CCC GTC
 P   G   E   D   G   R   P   G   P   P   G   P   Q   G   A   R   G   Q

>Hind_III_Site
                                |
                  >STOP        <<-3'_PCR_Primer_#_1010_[Split]
                    |           |
          6780      |   6790    |       6800
           *        |     *     |         *
       CCT GGT GTC ATG TAG AAG CTT GTC GTT GGA TGG
       GGA CCA CAG TAC ATC TTC GAA CAG CAA CCT ACC
        P   G   V   M   *   K   L   V   V   G   W
```

Figure 11 (continued)

RESTORATION OF HEARING LOSS

CROSS-REFERENCE TO RELATED APPLICATIONS

The present application is a U.S. National Phase Entry application of PCT/US2007/014391 filed Jun. 19, 2007, which claims priority to U.S. Provisional Patent Application No. 60/815,981 filed 22 Jun. 2006, which is incorporated herein by reference.

SEQUENCE LISTING

The instant application contains a Sequence Listing which has been submitted in ASCII format via EFS-Web and is hereby incorporated by reference in its entirety. Said ASCII copy, created Dec. 17, 2010, is named 69662403.txt and is 65,657 bytes in size.

FIELD OF THE INVENTION

The present invention relates to compositions and methods for restoring hearing loss. In particular, the invention relates to adoptive cellular therapies and DNA vaccines.

BACKGROUND OF THE INVENTION

Autoimmune diseases, particularly those that cause hearing loss such as Meniere's disease (MD), are common and often devastating diseases (Paparella, M. M., *The Natural Course of Meniere's Disease* in Meniere's Disease: Prospectives in the 90s (R. Filipo & M. Barbara eds. 1994) and Lachman, P. J., et al., Clinical Aspects of Immunology (1993)). The main feature of such diseases is the development and persistence of inflammatory processes in the apparent absence of pathogens, leading to destruction of the target tissues. A comprehensive explanation as to the onset or persistence of autoimmune ear diseases such as idiopathic progressive bilateral sensorineural hearing loss, Meniere's disease and other autoimmune inner ear diseases is not known yet known (Paparella, M. and Lachman, P. J., et al.).

Generally, chronic activation of helper T lymphocytes, reactive against self-proteins, appears to be crucial for fueling destructive autoimmune processes. However, antibodies against self proteins as well as molecularly mimicked microbial products are also implicated in some autoimmune diseases. Why certain individuals develop autoimmune diseases is not yet to determined, but genetic and environmental factors are most likely involved. In several autoimmune diseases the causative antigen(s) are not identified or characterized fully since several different self proteins or molecularly similar microbial proteins could be involved. Similarly, in Meniere's disease, several candidate antigens have been identified and used to develop animal models to study autoimmune hearing loss using, for example, type II collagen (CII) (Yoo, T. J., Stuart, J. M., et al., Science, vol. 217, p. 1153-55 (1982) and Yoo, T. J., Tomoda, K., et al., Annal. Otol. Rhinol. Laryngol., vol. 93 (suppl. 113), p. 3-5. (1984)), type IX collagen, c-raf protein (Cheng, K. C., et al., Annal. Otol. Rhinol. Laryngol., vol. 109 (12 Pt. 1), p. 1093-98 (1997)), Po protein (Matsuoka, H., Cheng, K. C., et al., Annals Oto. Rhino. Laryngol., vol. 108 (3), p. 255-64 (1998)) and most recently, β-tubulin (Yoo, T. J., Tanaka, H., et al. Meniere's Disease update, p. 529-535 (1999)).

Autoimmune disorders correspond to irregular immune responses directed at self-tissue. T cells play a central role in the initiation and perpetuation of organ-specific autoimmune disease (Harrison, L. C., Hafler, D. A., Current Opinion in Immunology, vol. 12(2), p. 704-11 (2000)). Because T cells are important mediators in the pathogenesis of autoimmune disease, they are ideal candidates for cell based gene therapy. Several models of autoimmunity involve a Th1-biased progression of immune responses against self antigens, probably responsible for much of the tissue destruction which occurs in autoimmune diseases. Numerous studies have demonstrated successful prevention or amelioration of autoimmune pathogenesis by blocking Th1 cytokines with specific antagonists or by counteracting the inflammatory response with regulatory cytokines (Harrison, L. C., Hafler, D. A.).

SUMMARY OF THE INVENTION

The present invention relates to compositions and methods for restoration of hearing loss. In particular aspects, hearing loss results from inflammation due to autoimmune disorders. In other particular aspects, the invention relates to DNA vaccines and adoptive cellular gene therapies to treat or ameliorate hearing loss.

In one aspect, the invention provides a method of treating or ameliorating hearing loss which includes administering a composition that reduces inflammation. In another aspect, the invention provides a method of treating or ameliorating hearing loss by administering a composition that reduces inflammation which includes an inflammatory response control element; preferably the inflammatory control element is a protein, nucleic acid or polynucleotide. In a related aspect, the invention also provides a method of treating or ameliorating hearing which includes administering two or more inflammatory response elements. In another aspect, the invention provides a method of manufacturing a composition for treatment or prophylaxis of autoimmune related hearing loss which includes preparing a polynucleotide or fragment thereof with a promoter/enhancer transcriptionally linked to a sequence encoding an inflammatory response control gene or fragment thereof. In a related aspect, the invention provides a method of preparing a composition for expression of an inflammatory response control polynucleotide or fragment thereof in a subject which includes preparing a polynucleotide with a promoter/enhancer transcriptionally linked to a sequence encoding an inflammatory response control gene or fragment thereof; preparing a transfection facilitating material; and combining the transfection facilitating material with the polynucleotide. The invention also provides compositions and methods for administration to a mammal, preferably a human. In another aspect, the invention provides a composition that includes a pharmaceutically acceptable carrier and a polynucleotide including a sequence encoding an inflammatory response control polypeptide. In other aspects, the invention provides a pharmaceutical kit which includes a container suitable for holding a pharmaceutical for administration to a subject; preferably a human, a polynucleotide including a sequence encoding an inflammatory response control polypeptide, a pharmaceutically acceptable carrier, and a label affixed to the container or a package insert. In yet other aspects, the invention provides administering a polypeptide homologous to a inflammatory response control polypeptide or fragment thereof.

In preferred embodiments of the above aspects of the invention, the composition that reduces inflammation of the methods and compositions may be a protein, nucleic acid or polynucleotide; preferably the polynucleotide and/or nucleic acid is DNA or RNA; preferably the polynucleotide is circular DNA; preferably the polynucleotide is a plasmid; preferably the polynucleotide includes a promoter/enhancer transcriptionally linked to the sequence encoding an inflammatory response control gene; preferably the polynucleotide includes an origin of replication (ORI); preferably the polynucleotide includes a multiple cloning site (MCS); preferably the promoter is suitable for expression in eukaryotic cells; in some preferable embodiments, the polynucleotide is a vector; preferably a viral vector; in other preferably embodiments, the polynucleotide is RNA; preferably the polynucleotide is double stranded RNA; preferably the polynucleotide is short interfering RNA (siRNA); or preferably more than one composition that reduces inflammation can be administered simultaneously.

In other preferred embodiments, the invention relates to administration of proteins and/or polypeptides of inflammatory response control polypeptides. In other embodiments, the invention relates to administration of nucleic acids, and/or polynucleotides encoding inflammatory response control polypeptides. The compositions are prepared and administered in such a manner that a inflammatory response control polypeptide is expressed in a subject to which the composition is administered. The compositions may include expression systems, delivery systems, and coding sequences of immunoregulatory genes such as anti-inflammatory cytokines, cytokine agonists or anti-TNF antibodies. Preferably, the inflammatory response control element of the methods and compositions increases a gene that decreases inflammation; preferably increasing gene expression is by up-regulating expression; preferably the gene that decreases inflammation is a Th2 cytokine; preferably the Th2 cytokine is IL-4, IL-5, IL-10, or IL-13; in other preferable embodiments, the inflammatory response control composition inhibits or attenuates a gene that increases inflammation; preferably the gene that increases inflammation is a Th1 cytokine; preferably attenuating gene expression is by down-regulating expression; preferably the Th1 cytokine is IL-2, IL-12, TNFα, or IFNγ, in some embodiments, the composition affects regulation by stimulating expression or producing a gene that decreases inflammation whereas in other embodiments, the composition affects regulation by inhibiting expression of a gene that increases stimulation such as a Th1 antagonist.

In certain preferred embodiments, the inflammatory response control element includes a gene or protein encoding an autoantigen, an autoimmune inflammation reducing cytokine, an antagonist to an autoimmune inflammation increasing cytokine, or a gene that induces anergy or fragments thereof; preferably, the inflammatory response control element is, or homologous to, IL-12p40, IL-4, IL-10, TGFβ, anti-TNFα-scFv, IL-5, and IL-13 or fragments thereof. In other preferred embodiments, autoantigens administered by DNA vaccine or adoptive cellular gene therapy can be used to treat hearing loss; preferably the autoantigens is, or homologous to type II collagen, cyanogen bromide peptide 11 (CB11) of type II collagen, cyanogen bromide peptide 9 (CB9) of type II collage, type IX collagen, c-raf protein, P0 protein, P30 protein, β-tubulin, and cochlin or fragments thereof. Autoantigens when normally immunized directly to a subject cause an autoimmune response such as an increase in inflammation. However, when the autoantigen is administered by methods such as adoptive cellular gene therapy or as a DNA vaccine, the autoantigen can treat an autoimmune response, for example by decreasing inflammation.

In other preferred embodiments, the composition reducing inflammation of the invention methods and compositions includes delivery by adoptive cellular gene therapy. Preferably, the type of cell used for adoptive cellular therapy is autologous or nonautologous; preferably the type of cell used for adoptive cellular gene therapy is a T cell, an antigen presenting cell, a fibroblast or a stem cell; preferably the type of cell used for adoptive cellular gene therapy is a dendritic cell, NIH3T3 cell, non-autologous stem cells such as cells from American Type Culture Collection or an autologous stem cell.

In certain embodiments, polynucleotides of the invention are administered to a patient with a pharmaceutically acceptable carrier. In certain embodiments, the polynucleotide includes a eukaryotic promoter. In certain embodiments, the polynucleotide is a plasmid complexed with a promoter/enhancer transcriptionally linked to a sequence encoding an inflammatory response control element. In certain embodiments, the polynucleotide is a viral vector. In certain embodiments, the polynucleotide is administered with a lipofection reagent. In certain embodiments, the methods of the present invention include one or methods of administering the composition selected from the group consisting of intravenously, intranasally, subcutaneously, by injection, by inhalation and by gene gun.

In certain preferred embodiments of the methods of the invention, the polynucleotide including a sequence encoding an inflammatory response control polypeptide or fragment thereof is administered to a mammal; more preferably the mammal is a human; preferably the polynucleotide including a sequence encoding an inflammatory response control gene or fragment thereof is administered with a transfection facilitating material; preferably the transfection facilitating material includes a lipid; preferably the polynucleotide is administered in a pharmaceutically acceptable carrier; in certain preferred embodiments the polynucleotide is administered by viral transduction; preferably the polynucleotide is administered by gene gun; preferably the polynucleotide is administered by inhalation; or preferably the polynucleotide is administered by injection, or preferably subcutaneous injection or more preferably intramuscular injection.

In certain preferred embodiments, the composition of the invention includes a polynucleotide including a sequence encoding an inflammatory response control polypeptide or fragment thereof; preferably the composition includes a pharmaceutically acceptable carrier; preferably the composition includes a transfection facilitating material, preferably the transfection facilitating material includes a lipid; preferably the composition is administered with an adjuvant; preferably the composition is suitable for injection into a mammal, preferably the mammal is a human; preferably the composition is suitable for inhalation by a mammal, preferably the mammal is a human; preferably the composition is enclosed in a pharmaceutically acceptable carrier, preferably the pharmaceutically acceptable carrier has a label indicating the contents therein and a statement regarding administration of the polynucleotide; preferably the composition includes a package insert, preferably the package insert includes statements regarding the contents of the composition, more preferably dosing information.

As used herein, the term "anergy" refers to loss or weakening of an immune response in response to an antigen. Anergy can be thought of as the opposite of allergy, which is an overreaction to a substance.

As used herein, the term "antigen" refers broadly to any composition to which an individual can generate an immune response. "Antigen" as used herein refers broadly to a molecule that contains at least one antigenic determinant to which the immune response may be directed. The immune response may be cell mediated or humoral or both. As well known in the art, an antigen may be protein in nature, carbohydrate in nature, lipid in nature, nucleic acid in nature, or combinations of these biomolecules. For example, an antigen may include non-natural molecules such as polymers and the like. Antigens include self antigens and foreign antigens such as antigens produced by another animal or antigens from an infectious agent. Infectious agent antigens may be bacterial, viral, fungal, protozoan, and the like.

As used herein, the term "autoantigen" refers to an antigen that stimulates the production of autoantibodies, as in an autoimmune reaction. Examples of autoantigens include, but are not limited to type II collagen, cyanogen bromide peptide 11 (CB11) of type II collagen, cyanogen bromide peptide 9 (CB9) of type II collage, type IX collagen, c-raf protein, P0 protein, P30 protein, β-tubulin, and cochlin, or fragments thereof.

As used herein, the terms "autoimmune" and "autoimmune related" refers to a state in which the immune system's tolerance to self is lost or impaired. Tolerance is the inability for an immune system to react to itself and therefore can identify and respond to foreign antigens. An overview of autoimmunity and cochlear disorders is provided in "Textbook of Audiological Medicine: Clinical Aspects of Hearing and Balance," p. 61-88 (Taylor & Francis Group, Independence, Ky., 2003).

As used herein, the term "autoimmune related inflammation" refers to inflammation caused by an autoimmune-associated disease such as Meniere's disease and Autoimmune Inner Ear Disease (AIED).

As used herein, the term "autologous" when used in referenced to cells removing cells from a subject, possible altering the cells or preserving the cells and reinfusing the cells back into the subject.

As used herein, the term "carrier" includes pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecule weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN, polyethylene glycol (PEG), and PLURONIC.

As used herein, the term "coding region" or "coding sequence" refers to a nucleic acid sequence, its complement, or a part thereof, which encodes a particular gene product or a fragment thereof for which expression is desired, according to the normal base pairing and codon usage relationships. Coding sequences include exons in genomic DNA or immature primary RNA transcripts, which are joined together by the cell's biochemical machinery to provide a mature mRNA. The anti-sense strand is the complement of such a nucleic acid, and the encoding sequence can be deduced from there. The coding sequence is placed in relationship to transcriptional control elements and to translational initiation and termination codons so that a proper length transcript will be produced and will result in translation in the appropriate reading frame to produce a functional desired product.

The term "complement" "complementary" or "complementarity" as used herein with reference to polynucleotides (i.e., a sequence of nucleotides such as an oligonucleotide or a target nucleic acid) according to standard Watson/Crick pairing rules. The complement of a nucleic acid sequence such that the 5' end of one sequence is paired with the 3' end of the other, is in "antiparallel association." For example, the sequence "5'-A-C-T-3'" is complementary to the sequence "3'-T-C-A-5'." Certain nucleotides not commonly found in natural nucleic acids may be included in the nucleic acids described herein; these include, for example, inosine, 7-deazaguanine, Locked Nucleic Acids (LNA), and Peptide Nucleic Acids (PNA). A complement sequence can also be a sequence of RNA complementary to the DNA sequence or its complement sequence, and can also be a cDNA. Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Complementarity may be "partial" in which only some of the nucleotide bases of two nucleic acid strands are matched according to the base pairing rules. Complementarity may be "complete" or "total" where all of the nucleotide bases of two nucleic acid strands are matched according to the base pairing rules. Complementarity may be absent where none of the nucleotide bases of two nucleic acid strands are matched according to the base pairing rules. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

As used herein, the term "substantially complementary" refers to two sequences that hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

As used herein, the term "dendritic cell" (DC) refers to an antigen presenting cell (APC) which can be derived from a hematopoietic stem cell. DC can be obtained from many lymphoid and non lymphoid tissues, as well as peripheral blood and bone marrow. Hematopoietic stem cells such as CD34+ cells in humans can be artificially differentiated into DC in vitro. The dendritic cell has a characteristic morphology with thin sheets (lamellipodia) extending from the dendritic cell body in several directions. Several phenotypic criteria are also typical, but can vary depending on the source of the dendritic cell. These include high levels of MHC molecules and costimulatory molecules (e.g., B7-1 and B7-2), a lack of markers specific for granulocytes, NK cells, B cells, and T cells. In the mouse, some (but not all) dendritic cells express 33D1 (DC from spleen and Peyer's patch, but not skin or thymic medulla), NLDC145 (DC in skin and T-dependent regions of several lymphoid organs and CD11C (Cd11c also reacts with macrophage). Dendritic cells are able to initiate primary T cell responses in vitro and in vivo. These responses are antigen specific. Dendritic cells direct a strong mixed leukocyte reaction (MLR) compared to peripheral blood leukocytes, splenocytes, B cells and monocytes.

As used herein, the term "expression" refers to the biological production of a product encoded by a coding sequence. In most cases a DNA sequence, including the coding sequence, is transcribed to form a messenger RNA (mRNA). Messenger-RNA is translated to form a polypeptide product which has biological activity. However in some cases, an RNA product may have the relevant activity and would thus be regarded as a gene product. Expression may involve further processing steps of the transcription RNA product, such as splicing to remove introns, and/or post-translational processing of a polypeptide product.

As used herein, the term "immunological tolerance" refers to the acquisition of unresponsiveness to self-antigens. The ability to differentiate self-antigens and non-self-antigens is essential to the preservation of the host. Immunological tolerance is further described in Seroogy, C. M., et al., Gene Therapy, vol. 7, p. 9-13 (2000); Costa, G. L., et al., J. Immunol., vol. 164, p. 3581-90 (2000); and (Weiner, H. L., et al., NY Acad. Sci., vol. 778, p. xiii-xviii (1996).

As used herein, the term "inflammatory response element" refers to any molecule that decreases inflammation. Preferably the inflammation is due to an autoimmune response. Preferably the molecule is a protein, peptide, polypeptide, nucleic acid, oligonucleotide, or polynucleotide. Some inflammatory response elements are well known in the art and include, but are not limited to molecules that can up-regulate or produce polypeptides that decrease autoimmune inflammation, which include but are not limited to polypeptides IL-4 (GenBank Accession No. M13982; SEQ ID NO:16) and IL-10 (GenBank Accession No. M57627; SEQ ID NO:18) and nucleic acids encoding IL-4 and IL-10 (SEQ ID NOs:1 and 3). Inflammatory response elements can also down-regulate or inhibit polypeptides that increase autoimmune inflammation, which include but are not limited to polypeptides IL-12p40 (GenBank Accession No. AF180563; SEQ ID NO:20) and TGFβ (GenBank Accession No. M60316; SEQ ID NO:21) and nucleic acids encoding IL-12p40 and TGFβ. Additional inflammatory response elements include anti-TNF antibodies (for example, GenBank Accession No. AF288521; SEQ ID NO:22). However, it is understood that other inflammatory response elements are subject to the invention, including those known in the art and those not yet identified. Preferably an inflammatory response polypeptide or fragment thereof, of the invention has an amino acid sequence that is homologous to an amino acid sequence of an inflammatory response element as provided herein, i.e., SEQ ID NOs:16-29. In certain preferred embodiments, a fragment of an inflammatory response element has at least 25 amino acids, more preferably at least 50 amino acids, more preferably at least 150 amino acids, more preferably at least 200 amino acids, more preferably at least 250 amino acids, more preferably at least 300 amino acids, more preferably at least 400 amino acids, more preferably at least 500 amino acids, more preferably at least 600 amino acids, more preferably at least 700 amino acids, more preferably at least 800 amino acids that are homologous to an inflammatory response element as provided herein, i.e., SEQ ID NOs:16-29. The term "homologous" as it refers herein to an amino acid sequence means that the amino acid is at least 70%, more preferably 75%, more preferably 80%, more preferably 85%, more preferably 90%, more preferably 95%, more preferably 98%, or most preferably 100% identical to a known amino acid sequence (for example SEQ ID NOs:16-29).

As used herein, the term "lipofection reagent" refers to a substance used to incorporate genetic material into a cell by means of liposomes. Examples of lipofection reagents include lipofectin, lipofectamine, cationic lipids and neutral co-lipids.

As used herein, the term "plasmid" refers to a construct made up of genetic material (i.e., nucleic acids). It includes genetic elements arranged such that an inserted coding sequence can be transcribed in eukaryotic cells. While the plasmid may include a sequence from a viral nucleic acid, such viral sequence does not cause the incorporation of the plasmid into a viral particle, and the plasmid is therefore a non-viral vector. Preferably a plasmid is closed circular nucleic acid. Preferably, nucleic acid is DNA or RNA. Preferably, plasmids may be introduced into cells by transformation and can replicate autonomously in the cell.

The term "replication origin" "origin of replication" as used herein refers to a nucleotide sequence at which DNA synthesis for the purpose of replicating the nucleic acid sequence begins. This is generally termed an ORI site. Circular bacteria generally have a single ORI site, whereas there can be many ORI sites on each eukaryotic chromosome. This term includes replicons, which as used herein refers to a genetic element that behaves as an autonomous unit during DNA replication. In bacteria, the chromosome functions as a single replicon, whereas eukaryotic chromosomes contain hundreds of replicons in series.

The term "transcription unit" or "expression cassette" refers to a nucleotide sequence which contains at least one coding sequence along with sequence elements which direct the initiation and termination of transcription. A transcription unit may however include additional sequences, which may include sequences involved in post-transcriptional or post-translational processes.

As used herein, the term "transcriptional control sequence" refers to a sequence which controls the rate of transcription of a transcriptionally linked coding region. The term can include elements such as promoters, operators, and enhancers. Preferably, the transcriptional control sequences will include at least one promoter sequence.

As used herein, the term "transcriptionally linked" refers to a system suitable for transcription, transcription will initiate under the direction of a control sequence and proceed through sequences which are transcriptionally linked with that control sequence. Preferably, no mutation is created in the resulting transcript which would alter the resulting translation product. For example, "transcriptionally linked" generally means that the DNA sequences being linked are contiguous, and, in the case of a secretory leader, contiguous and in reading phase. However enhancers do not have to be contiguous. Linking is accomplished by ligation at convenient restriction sites. If such sites do not exist, synthetic oligonucleotide adapters or linkers can be used in accordance with conventional practice.

As used herein, the term "5' untranslated region" or "5' UTR" refers to a sequence located 3' to promoter region and 5' of the downstream coding region. Thus, such a sequence, while transcribed, is upstream (i.e. 5') of the translation initiation codon and therefore is generally not translated into a portion of the polypeptide product.

As used herein, the term "3' untranslated region/poly (A) signal" or "3' UTR poly (A) signal" is a sequence located downstream (i.e., 3') of the region encoding material polypeptide. As with the 5' UTR, this region is generally transcribed but not translated. For expression in eukaryotic cells it is generally preferable to include a sequence which signals the addition of a poly-A tail. As with other synthetic genetic elements a synthetic 3' UTR/poly (A) signal has a sequence which differs from naturally-occurring, UTR elements.

As used herein, the term "cytomegalovirus promoter/enhancer sequences" refers to sequences from a cytomegalovirus which are functional in eukaryotic cells as a transcriptional promoter and an upstream enhancer sequence. The enhancer sequence allows transcription to occur at a higher frequency from the associated promoter.

For the plasmids described herein, one or more of a promoter, 5' untranslated region (5' UTR), 3' UTR/poly (A) signal, and introns may be a synthetic sequence. In this context the term "synthetic" refers to the sequence that is not provided directly by the sequence of a naturally occurring genetic element of that type but rather is an artificially created sequence (i.e., created by an individual by molecular biological methods). While one or more portions of such a synthetic sequence may be the same as portions of naturally occurring sequences, the full sequence over the specified genetic element is different from a naturally occurring genetic element of that type. The use of such synthetic genetic elements allows the functional characteristics of that element to be appropriately designed for the desired function.

As used herein, a polynucleotide including a sequence encoding an inflammatory response polypeptide or fragment thereof refers to a polynucleotide with a nucleotide sequence that encodes a gene capable of decreasing inflammation as defined herein. It is understood that there are many different nucleotide sequences that could encode a single polypeptide sequence based on normal base paring and codon usage relationships. As such, the term refers to any nucleic acid sequence that would encode an inflammatory response control element or fragment thereof. In certain preferred embodiments the polynucleotide including a polynucleotide including a sequence encoding an inflammatory response polypeptide or fragment thereof of the invention includes a nucleotide sequence that encodes a protein homologous to IL-12p40, IL-4, IL-10, TGFβ, anti-TNFα-scFv, IL-5, or IL-13. Preferably a polynucleotide including a sequence encoding an inflammatory response polypeptide or fragment thereof includes a contiguous segment of at least 50 nucleotides; more preferably at least 100 nucleotides; more preferably at least 300 nucleotides; more preferably at least 600 nucleotides; more preferably at least 1,000 nucleotides; more preferably at least 1,500 nucleotides; more preferably at least 2,000 nucleotides that are homologous to a sequence encoding polypeptides IL-12p40, IL-4, IL-10, TGFβ, and anti-TNFα-scFv (as shown in SEQ ID NOs:1-15. The term "homologous" as it refers herein to an nucleotide sequence means that the nucleotide sequence is at least 70%, more preferably 75%, more preferably 80%, more preferably 85%, more preferably 90%, more preferably 95%, more preferably 98%, or most preferably 100% identical to a known nucleotide sequence (for example sequences encoding for IL-12p40, IL-4, IL-10, TGFβ and anti-TNFα-scFv as provided in SEQ ID NOs: 1-15). It is understood that a polynucleotide including a sequence encoding an inflammatory response control polypeptide can contain additional nucleotides, other than the nucleotides forming a sequence that encode an inflammatory response element.

As used herein, the term "sample" or "test sample" refers to any liquid or solid material believed to comprise nucleic acids of interest. A test sample may be obtained from any biological source (i.e., a biological sample), such as cells in culture or a tissue sample or synthetically produced including a chemically synthesized template.

As used herein, the term "sequence encoding an inflammatory response gene or fragment thereof" refers to any nucleic acid sequence encoding an inflammatory response gene or a fragment thereof. An inflammatory response gene refers to a polynucleotide that encodes an amino acid sequence corresponding to a polypeptide which may cause inflammation. Examples of inflammatory response genes include, but are not limited to IL-12p40, IL-4, IL-10, TGFβ, anti-TNFα-scFv, IL-5, and IL-13. Preferably the inflammatory response gene of the invention encodes a peptide with an amino acid sequence corresponding to the amino acid sequence of any of the inflammatory response polypeptide or a fragment thereof based on the normal base pairing and translational codon usage relationships. Preferably, the coding sequence encodes the exact, full amino acid sequence of natural inflammatory response gene.

As used herein, the term "transduced" refers to a cell with a selected nucleic acid translocated into the cell. A cell is "stably transduced" with a selected nucleic acid when the selected nucleic acid is replicated and passed on to progeny cells. A cell is "transformed" with a selected nucleic acid when the selected nucleic acid is integrated into the cell's genome.

As used herein, the terms "treating," "treatment," and "therapy" refer to curative therapy, prophylactic therapy, and preventive therapy. An example of "preventive therapy" or "prophylactic therapy" is the prevention or lessened targeted pathological condition or disorder. Those in need of treatment include those already with the disorder as well as those prone to have the disorder or those in whom the disorder is to be prevented. Administration can be "chronic" administration which refers to administration of the agent(s) in a continuous mode as opposed to an acute mode, so as to maintain the initial therapeutic effect (activity) for an extended period of time. Administration can also be "intermittent" administration which is treatment that is not consecutively done without interruption but, rather, is cyclic in nature. Administration can also be "in combination with" one or more further therapeutic agents includes simultaneous (concurrent) and consecutive administration in any order.

As used herein, the term "up-regulate" refers to the expression of a gene, or level of RNA or equivalent RNA encoding one or more protein subunits, or activity of one or more protein subunits, such as Th2 cytokines, is greater than that observed in the absence of the compositions of the invention. For example, the expression of a gene, such as Il-4, can be increased in order to treat, prevent, ameliorate, or modulate a pathological condition caused or exacerbated by an absence or low level of gene expression.

As used herein, the term "inhibit" or "down-regulate" refers to the expression of a gene, or level of RNA or equivalent RNA encoding one or more protein subunits, or activity of one or more protein subunits, such as Th1 cytokines, is reduced below that observed in the absence of the nucleic acid molecules of the invention. In one embodiment, inhibition or down-regulation with enzymatic nucleic acid molecule preferably is below that level observed in the presence of an enzymatically inactive or attenuated molecule that is able to bind to the same site on the target RNA, but is unable to cleave that RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of IL-2 with the compositions of the instant invention is greater in the presence of the composition than in its absence.

As used herein, the term "about" means in quantitative terms plus or minus 10% of the indicated value.

Other features and advantages of the invention will be apparent from the following description of the preferred embodiments and from the claims.

BRIEF DESCRIPTION OF THE FIGURES

FIG. 11. CB 11 peptide of type II collagen DNA Sequence Range: 5910 to 6806 (DNA sequence disclosed as SEQ ID NO: 30. Protein sequences disclosed as SEQ ID NOs: 31-32, respectively., in order of appearance).

DETAILED DESCRIPTION OF THE INVENTION

Figure 1:
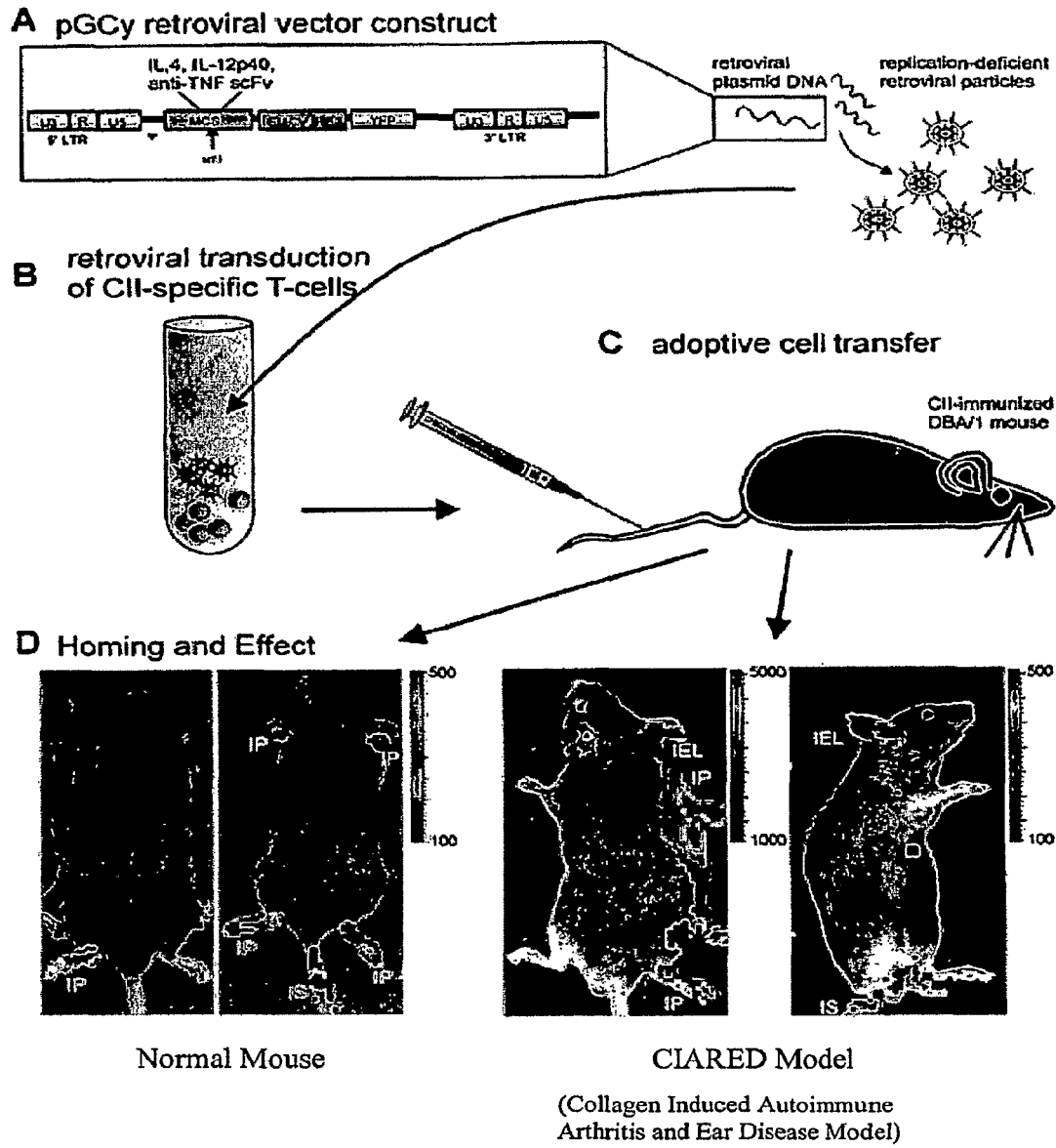
FIG. 1. Schematic drawing of adoptive cellular gene therapy strategy.

The present invention relates to compositions and methods for treating or ameliorating hearing loss. In particular aspects, the invention relates to the administration to a mammal of a composition encoding an inflammatory response control element. The compositions are prepared and administered in such a manner that the inflammatory response coding sequence is expressed in the mammal to which the composition is administered. These compositions include expression systems, delivery systems, and certain inflammatory response genes and proteins.

Allergic diseases have an immune response that deviates toward a T-helper type 2 (Th2) profile and away from the T-helper type 1 (Th1) profile. The Th1 profile is characterized by increased levels molecules that perpetuate an inflammatory response such as IFN-γ and IL-2. The Th2 profile is characterized by increased levels of particular interleukins (IL), such as IL-4, IL-5, IL-10, IL-13, CD4+ T cells and the production of antigen specific IgE. IL-4 is important in IgE synthesis and development of the Th2 response, and IL-5 in eosinophil survival. Immunotherapy results in reversal of this imbalance, with increases in Th1 cytokines, IFN-γ and IL-12, which in turn inhibit the Th2 response. At the same time that genetic vaccination work is burgeoning, so is the work on the low affinity IgG receptor, FCγRIIB, which when occupied, inhibits the IgE-mediated response on mast cells and basophils (Daeron, et al., J. Clin. Invest. 95(2): 577-85 (1995)).

Systematic administration of TGFβ, IL-4 or IL-10 serve as effective therapies in models of autoimmune disease such as collagen-induced arthritis (CIA) (Horsfall, A. C., et al., J. Immunol., vol. 159, p. 5687-96 (1997) and Garcia G., et al., J Autoimmunity, vol. 13, p. 315-24 (1999)), experimental autoimmune encephalomyelitis (EAE) (Racke, M. K., et al., J. Exp. Med., vol. 18, p. 1961-66 (1994) and Inobe, J., et al., Eur. J. Immunol., vol. 28, p. 278-79 (1998)) and non-obese diabetic mice (NOD) (Tominaga, Y., et al., Clin. Immunopathol., vol. 86, p. 209-18 (1998)). These protocols appear to work by shifting the cytokine balance away from Th1 dominance. Cytokine-induced immune deviation has been investigated as potential therapy for autoimmune diseases, as cytokine present at time of activation may alter the pathogenicity of effector T cells (Racke, M. K., et al.). However, apart from site-specific transgenic expression of these cytokine genes, cytokine therapy has required systemic administration, which can lead to deleterious side effects (Leach, M. W., et al., Clin. Immunol. Immunopathol., vol. 83, p. 8-11 (1997). Therefore, approaches have been taken to investigate targeting cytokine delivery to the site of inflammation as alternative to systemic therapeutic regimes (Tamer, I. H., et al., Curr. Opinion Immunol., vol. 13 (21), p. 676-82 (2001)).

In some embodiments, compositions that reduce inflammation can affect regulation by stimulating expression or producing a gene that decreases inflammation whereas in other embodiments, the composition can affect regulation by inhibiting expression of a gene that increases stimulation such as an antagonist. Double stranded RNA, in particular siRNA can be used for inhibiting expression. RNA can be introduced into a living cell to inhibit gene expression of a target in that cell. The process may be done ex vivo or in vivo. Such RNA compositions and methods of use are further described, for example, in U.S. Pat. No. 6,506,559.

Various approaches are used to introduce DNA into host cells, including naked DNA, DNA complexed with liposomes and various viral vectors. Naked polynucleotide materials, methods, and delivery systems are used, such as those described in U.S. Pat. Nos. 6,040,295, 5,763,270, and 5,580, 859. Polynucleotides are naked in the sense that they are free from any delivery vehicle that can act to facilitate entry into the cell or any material which promotes transfection, such as liposomal formulations, charged lipids such as lipofectin or precipitating agents such as $CaPO_4$.

Vectors for delivering nucleic acids can be viral, non-viral, or physical. See, for example, Rosenberg et al., Science, 242:1575-1578 (1988), and Wolff et al., Proc. Natl. Acad. Sci. USA 86:9011-9014 (1989). Recent reviews discussing methods and compositions for use in gene therapy include Eck et al., in Goodman & Gilman's The Pharmacological Basis of Therapeutics, Ninth Edition, Hardman et al., eds., McGray-Hill, New York, (1996), Chapter 5, pp. 77-101; Wilson, Clin. Exp. Immunol. 107 (Suppl. 1):31-32 (1997); Wivel et al., Hematology/Oncology Clinics of North America, Gene Therapy, S. L. Eck, ed., 12(3):483-501 (1998); Romano et al., Stem Cells, 18:19-39 (2000), and the references cited therein. U.S. Pat. No. 6,080,728 also provides a discussion of a wide variety of gene delivery methods and compositions. The routes of delivery include, for example, systemic administration and administration in situ. Well-known viral delivery techniques include the use of adenovirus, retrovirus, lentivirus, foamy virus, herpes simplex virus, and adeno-associated virus vectors.

Viral vectors can also be used for transfection of a mammalian cell and introducing a polynucleotide into a genome. In an indirect method, viral vectors, carrying new genetic information, are used to infect target cells removed from the body, and these cells are then re-implanted. Direct in vivo gene transfer into postnatal animals has been reported for formulations of DNA encapsulated in liposomes and DNA encapsulated in proteoliposomes containing viral envelope receptor proteins (Nicolau et al., Proc. Natl. Acad. Sci. USA 80:1068-1072 (1983); Kaneda et al., Science 243:375-378 (1989); Mannino et al., Biotechniques 6:682-690 (1988). Viral vectors can be injected or transduced into host cells in vitro, which are then adoptively transferred and serve as delivery vehicles, such as T cells (Nakajima, A., et al., J. Clin. Invest., vol. 17(21), p. 1293-1310 (2001) and Tuohy, V. K., et al., J. Neuroimmunol., vol. 17(2), p. 226-32 (2000)), fibroblasts (Rabinovich, G. A., et al., J. Exp. Med., vol. 19, p. 385-98 (1999)), dendritic cells (DCs) (Kim, S. H., et al., J. Immunol., vol. 166(21), p. 3499-3550 (2001) and Morita, Y., et al., J. Clin. Invest., vol. 17(21), p. 1275-84 (2001)) and stem cells (ATCC or autolougous).

Adoptive Cellular Gene Therapy

The techniques for introducing nucleic acids into cells vary depending upon whether the nucleic acid is transferred into cultured cell in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A preferred in vivo gene transfer techniques include transfection with viral (typically, retroviral) vectors and viral coat protein-liposome mediated transfection (Dzau, et al., Trends in Biotechnology 11(5):205-10 (1993)). Suitable vectors can be constructed by any of the methods well known in the art. See, for example, Sambrook et al., Molecular Cloning, A Laboratory Manual, Second Edition, Cold Spring Harbor Press (1989), and Ausubel et al., eds., Current Protocols in Molecular Biology, John Wiley & Sons, N.Y. (1987 and updates). The use of cationic liposomes, such as the CD-Chol/DOPE liposome, has been widely documented as an appropriate vehicle to deliver DNA to a wide range of tissues through intravenous injection of DNA/cationic liposome complexes. See Caplen et al., Nature Med., 1:39-46 (1995); Zhu et al., Science, 261:209-211 (1993). Liposome transfer of genes to target cells by fusing with the plasma membrane. Examples of the successful application of liposome complexes include those of Lesson-Wood et al., Human Gene Therapy, 6:395-405 (1995), and Xu et al., Molecular Genetics and Metabolism, 63:103-109 (1998).

Nucleic acid is delivered to the site of the injury in an individual by any of various means known in the art. For example, the nucleic acid source may be combined with an agent that targets cells in the damaged tissue, such as an antibody specific for a cell surface membrane protein or the target cell, a ligand for a receptor on the target cells, etc. Where liposomes are employed, proteins which bind to a cell surface membrane protein associated with endocytosis may by used for targeting and/or to facilitate uptake, e.g., capsid proteins or fragments thereof trophic for a particular cell type, antibodies for proteins which undergo internalization in cycling, proteins that target intracellular localization and enhance intracellular half-life. The technique of receptor-mediated endocytosis is described, for example, by Wu, et al., J. Biol. Chem. 262(10):4429-32 (1987); and Wagner, et al., Proc. Natl. Acad. Sci. USA 87(9):3410-4 (1990). For a review of gene marking and gene therapy protocols, see Anderson, Science 256(5058):808-13 (1992).

The methods and compositions of the present invention can also be utilized in adoptive cellular gene therapy using genetically engineered immune cells, such as primary T cells, dendritic cells, fibroblasts, and stem cells, that have the ability to migrate to sites of inflammation in organ-specific autoimmune disease to express and deliver immunoregulatory products and/or therapeutic gene products after ex vivo viral transduction. Ex vivo transduction of these cells avoids systemic exposure of the host to the transgene-encoding vector and thus adds to the safety of this approach. Antigen-specific T cell hybridomas were used which expressed anti-inflammatory cytokines such as IL-4, cytokines antagonists such as IL-12 receptor antagonist IL-12p40 or an anti-TNF antibody single chain variable fragment (scFv). All these molecules inhibited disease development and reduced disease severity. CIA models of adoptive cellular gene therapy are examples of convenient gene shuttles for mediating anti-inflammatory gene therapy. Additional studies showed that primary T cells which are more difficult to transducer, are equally effective when expressing IL-12p40, indicating that successful adoptive cellular gene therapy may be applied independent of the cell type used. Therefore, cells such as bone-marrow derived dendritic cells (DCs) can be used to migrate to inflammation sites.

Cells of the dendritic family are especially suited to perform two distinct functions at two discrete locations. In the peripheral tissues, dendritic cells (DC) act as sentinels for "dangerous" antigens. DCs migrate and transport antigens to the lymphoid organ, where they initiate activation of T lymphocytes which are specific for the antigen. During migration, DCs shift from an antigen-capturing mode to a T cell sensitizing mode. DCs also influence the character of T cell differentiation, i.e., the Th1/Th2 balance. DCs provide antigenic and costimulatory signals required for optimal activation of T lymphocytes. DCs and methods of use are further described, for example, in U.S. Pat. No. 6,734,014.

Stem cells may also be used for adoptive cellular gene therapy. Preferably, human embryonic stem (ES) cells used for the invention. ES cells are cultured cell lines derived from inner cell masts of a blastocyst which can be grown indefinitely in an undifferentiated state, yet are also capable of differentiating into all cells of the adult body. Preferably, stem cells appropriate for use in the invention are derived from the subject themselves or are engineered in a way to circumvent an immune reaction, such as nuclear transfer or somatic cell nuclear transfer, which entails replacing embryonic stem cell DNA with a subject's DNA. Embryonic stem cells are the most versatile stem cell due to the ability to differentiate into the approximately 200 different cell types found in the adult human body and the only stem cell type for which routine genetic engineering protocols have been developed. Methods of generating stem cells ex vivo are well known in the art and include U.S. Pat. Nos. 6,326,198; 6,261,549; 6,093,531; 5,935,565; 5,670,351; 5,670,147; 5,646,043; 5,437,994.

Vaccination with cDNA requires fewer injections, and has a quicker build-up phase. The risk of adverse reactions to immunotherapy may also be reduced. Plasmid DNA and its gene expression have been noted to be long lasting (Wolff, et al., Hum. Mol. Genet. 1:363-69 (1992)) and immune responses in primates and rodents have been documented to last for more than one year following DNA vaccination (Donnelly, et al., J Immunol Meth. 176:145-152 (1994); and Raz, et al., Pro. Natl. Acad. Sci. 91:9519-9523 (1994)). It does not appear that plasmid DNA is incorporated into the host genome, but remains as an episome (Tang, et al., Nature. 356:152-4 (1992)). The discovery that naked DNA and RNA is taken up and transiently expressed by muscle cells in vivo has increased interest in using non-viral vehicles for genetic delivery. See Wolff et al., Science, 247, 1465-1468 (1990); Acsadi, et al., Nature, 352, 815-818, (1991). Although naked DNA and RNA can be taken up by mammalian cells, the efficiency of transfection is increased tremendously if the DNA or RNA is complexed in liposomes (Chen, et al., Gene Therapy 7(19): 1698-705 (2000)).

Administering a polynucleotide to a mammal in vivo, such that an inflammatory response element or fragment thereof is expressed in the mammal, can be achieved using any of many methods known in the art for mammalian gene expression. For example such methods for administering expressible polynucleotides to mammals including expression systems and delivery systems can be found in U.S. Pat. Nos. 6,875,748, 5,763,270, 5,580,859, 6,040,295, and 6,034,072.

Polynucleotide constructs described herein include nucleotide sequences encoding an inflammatory response element or fragment thereof. The polynucleotide is administered such that the polynucleotide is incorporated into cells and expresses a detectable amount of a prophylactically or therapeutically effective amount of a desired inflammatory response element or fragment thereof. Exemplary inflammatory response element suitable for use in the present invention include IL-12p40, IL-4, IL-10, TGFβ, anti-TNFα-scFv, IL-5, and IL-13.

Expression Systems

Non-viral administration of nucleic acid in vivo has been accomplished by a variety of methods. These include lipofectin/liposome fusion: Proc. Natl. Acad. Sci. 84, pp. 7413-7417 (1993); polylysine condensation with and without adenovirus enhancement: Human Gene Therapy 3, pp. 147-154 (1992); and transferrin:transferrin receptor delivery of nucleic acid to cells: Proc. Natl. Acad. Sci. 87, pp. 3410-3414 (1990). The use of a specific composition consisting of polyacrylic acid has been disclosed in WO 94/24983. Naked DNA has been administered as disclosed in WO90/11092.

Thus, in one aspect, the invention provides a plasmid for expression of inflammatory response control element or fragment thereof which includes an expression cassette, which can also be referred to as a transcription unit. When a plasmid of the present invention is placed in an environment suitable for gene expression, the transcriptional unit will thus express the polynucleotide including a sequence encoding an inflammatory response control or fragment thereof. The transcription unit includes a transcriptional control sequence, which is transcriptionally linked with inflammatory response control coding sequence. Transcriptional control sequence may include promoter/enhancer sequences such as cytomegalovirus (CMV) promoter/enhancer sequences. However, those skilled in the art will recognize that a variety of other promoter sequences suitable for expression in eukaryotic cells are known and can similarly be used in the constructs of this invention. The level of expression of the gene product will depend on the associated promoter and the presence and activation of an associated enhancer element. In certain embodiments, a sequence encoding a inflammatory response control gene or fragment thereof of the invention can be cloned into an expression plasmid which contains the regulatory elements for transcription, translation, RNA stability and replication (i.e. including a transcriptional control sequence). Such expression plasmids are well known in the art and one of ordinary skill would be capable of designing an appropriate expression construct with a polynucleotide including a sequence encoding an inflammatory response control element or fragment thereof in such a manner that the inflammatory response control element is expressible. There are numerous examples of suitable expression plasmids into which a polynucleotide including a sequence encoding a inflammatory response control gene or fragment thereof could be cloned such as pUMVC.

Large quantities of a bacterial host harboring a plasmid for expression of inflammatory response control element or fragment thereof may be fermented and the plasmid may be purified for subsequent use. Current human clinical trials using plasmids utilize this approach. Recombinant DNA Advisory Committee Data Management Report, Human Gene Therapy 6: 535-548 (1994).

The purpose of the plasmid is to generally be used in human gene therapy for the efficient delivery of nucleic acid sequences to and expression of therapeutic genes (i.e. inflammatory response control elements) in a cell or tissue of a mammal. In particular, the purpose of the plasmid is to achieve high copy number, avoid potential causes of plasmid instability and provide a means for plasmid selection. As for expression, the nucleic acid cassette contains the necessary elements for expression of the nucleic acid within the cassette. Expression includes the efficient transcription of an inserted gene, nucleic acid sequence, or nucleic acid cassette with the plasmid. Expression products may be proteins, polypeptides or RNA. The nucleic acid sequence can be contained in a nucleic acid cassette. Expression of the nucleic acid can be continuous or regulated.

As an initial step in the process of ultimately obtaining expression of a product encoded by a nucleic acid, is to effect the uptake of the nucleic acid by cells. Uptake of nucleic acid by cells is dependent on a number of factors, one of which is the length of time during which a nucleic acid is in proximity to a cellular surface. For instance, after intramuscular (i.m.) administration of plasmid DNA in buffer, a marked reduction in gene expression is observed if the muscle is massaged, presumably due to DNA leakage out of the muscle either directly or via lymphatic vessels (Human Gene Therapy 4:151-159; 1993). Accordingly, it would be desirable to formulate nucleic acids with compounds which would retard the rate at which nucleic acids diffuse or are carried away from a site at which cellular uptake of the nucleic acid is desired. Further, these compounds would be suitable for administration to an organism by means such as injection while maintaining or regaining the physical characteristics necessary to increase cellular uptake of nucleic acids.

Pharmaceutical Compositions

A composition comprising a polynucleotide including a sequence encoding an inflammatory response control element or fragment thereof can be administered as a pharmaceutical composition wherein the invention compound is formulated with a pharmaceutically acceptable carrier as is well known in the art. Techniques for formulation and administration may be found, for example, in "Remington's Pharmaceutical Sciences," (18th ed., Mack Publishing Co., Easton, Pa., 1990). Accordingly, the invention compounds may be used in the manufacture of a medicament. Pharmaceutical compositions of the invention compounds may be formulated as solutions or lyophilized powders for parenteral administration. Powders may be reconstituted by addition of a suitable diluent or other pharmaceutically acceptable carrier prior to use. Powders also may be sprayed in dry form. The liquid formulation may be a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride or sodium citrate.

Alternately, compositions comprising a polynucleotide including a sequence encoding a inflammatory response control element or fragment thereof may be encapsulated, tableted or prepared in a emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. For aqueous compositions used in vivo, the use of sterile pyrogen-free water is preferred. Such formulations will contain an effective amount of a polynucleotide together with a suitable amount of an aqueous solution in order to prepare pharmaceutically acceptable compositions suitable for administration to a mammal, preferably a human. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. For rectal administration, the invention compounds may be combined with excipients such as cocoa butter, glycerin, gelatin or polyethylene glycols and molded into a suppository.

Administration of pharmaceutically acceptable salts of the polynucleotides described herein is included within the scope of the invention. Such salts may be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like. For a helpful discussion of pharmaceutical salts, see S. M. Berge et al., Journal of Pharmaceutical Sciences 66:1-19 (1977).

The present invention also provides pharmaceutical product for use in supplying a inflammatory response control polypeptide to a mammal, comprising a pharmaceutically effective amount of a polynucleotide including a sequence encoding an inflammatory response control element or fragment thereof, a container enclosing the carrier and the polynucleotide in a sterile fashion, and means associated with the container for permitting transfer of the polynucleotide from the container to the interstitial space of a tissue, whereby cells of the tissue can take up and express the polynucleotide. The means for permitting such transfer can include a conventional septum that can be penetrated, e.g., by a needle. Alternatively, when the container is a syringe, the means may be considered to comprise the plunger of the syringe or a needle attached to the syringe. Containers used in the present invention may have at least 1, preferably at least 5 or 10, and more preferably at least 50 or 100 micrograms of polynucleotide, to provide one or more unit dosages. For many applications, the container will have at least 500 micrograms or 1 milligram, and often will contain at least 50 or 100 milligrams of polynucleotide.

The present invention also includes a pharmaceutical product, comprising a polynucleotide including a sequence encoding an inflammatory response control or fragment thereof, in physiologically acceptable administrable form, in a container, and a notice associated with the container in form prescribed by a governmental agency regulating the manufacture, use, or sale of pharmaceuticals, which notice is reflective of approval by the agency of the form of the polynucleotide for human or veterinary administration. Such notice, for example, may be the labeling approved by the U.S. Food and Drug Administration for prescription drugs, or the approved product insert. An example of packaging for the pharmaceutical product can be found in Example 7.

Polynucleotides including a sequence encoding an inflammatory response control element or fragment thereof for injection, a preferred route of delivery, may be prepared in unit dosage form in ampules, or in multidose containers. The polynucleotides may be present in such forms as suspensions, solutions, or emulsions in oily or preferably aqueous vehicles. Alternatively, the polynucleotide salt may be in lyophilized form for reconstitution, at the time of delivery, with a suitable vehicle, such as sterile pyrogen-free water. Both liquid as well as lyophilized forms that are to be reconstituted will comprise agents, preferably buffers, in amounts necessary to suitably adjust the pH of the injected solution. For any parenteral use, particularly if the formulation is to be administered intravenously, the total concentration of solutes should be controlled to make the preparation isotonic, hypotonic, or weakly hypertonic. Nonionic materials, such as sugars, are preferred for adjusting tonicity, and sucrose is particularly preferred. Any of these forms may further comprise suitable formulatory agents, such as starch or sugar, glycerol or saline. The compositions per unit dosage, whether liquid or solid, may contain from 0.1% to 99% of polynucleotide material.

The units dosage ampules or multidose containers, in which the polynucleotides are packaged prior to use, may comprise an hermetically sealed container enclosing an amount of polynucleotide or solution containing a polynucleotide suitable for a pharmaceutically effective dose thereof, or multiples of an effective dose. The polynucleotide is packaged as a sterile formulation, and the hermetically sealed container is designed to preserve sterility of the formulation until use.

The container in which the polynucleotide including a sequence encoding an inflammatory response control element or fragment thereof is packaged is labeled, and the label bears a notice in the form prescribed by a governmental agency, for example the Food and Drug Administration, which notice is reflective of approval by the agency under Federal law, of the manufacture, use, or sale of the polynucleotide material therein for human administration.

Federal law requires that the use of pharmaceutical agents in the therapy of humans be approved by an agency of the Federal government. Responsibility for enforcement is the responsibility of the Food and Drug Administration, which issues appropriate regulations for securing such approval, detailed in 21 U.S.C. §301-392. Regulation for biologic material, comprising products made from the tissues of animals is provided under 42 U.S.C. §262. Similar approval is required by most foreign countries. Regulations vary from country to country, but individual procedures are well known to those in the art.

The dosage to be administered depends to a large extent on the condition and size of the subject being treated as well as the frequency of treatment and the route of administration. Regimens for continuing therapy, including dose and frequency may be guided by the initial response and clinical judgment. The parenteral route of injection into the interstitial space of tissues is preferred, although other parenteral routes, such as inhalation of an aerosol formulation, may be required in specific administration, as for example to the mucous membranes of the nose, throat, bronchial tissues or lungs. An example of dosage administration if provided in Example 6.

As such, the invention provides a pharmaceutical product, comprising a polynucleotide including a sequence encoding an inflammatory response control element or fragment thereof, in solution in a physiologically acceptable injectable carrier and suitable for introduction interstitially into a tissue to cause cells of the tissue to express an inflammatory response control element or fragment thereof, a container enclosing the solution, and a notice associated with the container in form prescribed by a governmental agency regulating the manufacture, use, or sale of pharmaceuticals, which notice is reflective of approval by the agency of manufacture, use, or sale of the solution of polynucleotide for human administration.

Administration

In any of the methods disclosed herein, it is preferred that the composition comprising polynucleotide including a sequence encoding an inflammatory response control element or fragment thereof be delivered to a mammal. More preferably, the mammal is a human. Administration of the compositions of the present invention according to any of the above methods can be accomplished according to any of various methods known in the art. For example, U.S. Pat. No. 5,676,954 discloses injection of genetic material, complexed with cationic lipid carriers, into mice. Also, U.S. Pat. Nos. 5,589,466, 5,693,622, 5,580,859, 5,703,055, and PCT international patent application PCT/US94/06069 (WO 94/29469), provide methods for delivering compositions comprising naked DNA or DNA cationic lipid complexes to vertebrates.

In preferred embodiments, the compound comprising a polynucleotide including a sequence encoding an inflammatory response control element or fragment thereof can be administered parenterally, such as intravascularly, intravenously, intraarterially, intramuscularly, subcutaneously, or the like. The compound can be introduced into muscle, skin, brain, lung, liver or spleen tissue. The compound can also be introduced into the blood. Administration can also be orally, nasally, rectally, transdermally or inhalationally via an aerosol. The composition may be administered as a bolus, or slowly infused.

The polynucleotide including a sequence encoding an inflammatory response control element or fragment thereof may be delivered to the interstitial space of tissues of the animal body, including those of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts.

In vivo, muscle cells are particularly competent in their ability to take up and express polynucleotides. This ability may be due to the singular tissue architecture of muscle, comprising multinucleated cells, sarcoplasmic reticulum, and transverse tubular system. Polynucleotides may enter the muscle through the transverse tubular system, which contains extra cellular fluid and extends deep into the muscle cell. It is also possible that the polynucleotides enter damaged muscle cells which then recover.

Muscle is also advantageously used as a site for the delivery and expression of polynucleotides in a number of therapeutic applications because animals have a proportionately large muscle mass which is conveniently accessed by direct injection through the skin; for this reason, a comparatively large dose of polynucleotides can be deposited in muscle by multiple injections, and repetitive injections, to extend therapy over long periods of time, are easily performed and can be carried out safely and without special skill or devices.

Tissues other than those of muscle may also be advantageously used as injection sites to produce inflammatory response control elements of the invention. One such condition is the use of a polynucleotide to provide a polypeptide which to be effective must be present in association with cells of a specific type; for example, the cell surface receptors of liver cells associated with cholesterol homeostasis. (Brown and Goldstein, Science 232:34-47 (1986)). In this application, and in many others, such as those in which an enzyme or hormone is the gene product, it is not necessary to achieve high levels of expression in order to effect a valuable therapeutic result.

In certain embodiments, the polynucleotide including a sequence encoding an inflammatory response control element or fragment thereof is introduced into tissues using the injectable carrier alone. The carrier preferably is isotonic, hypotonic, or weakly hypertonic, and has a relatively low ionic strength, such as provided by a sucrose solution. The preparation may further advantageously comprise a source of a cytokine which is incorporated into liposomes in the form of a polypeptide or as a polynucleotide.

Compounds comprising a polynucleotide including a sequence encoding an inflammatory response control element or fragment thereof of the present invention may be formulated to include other medically useful drugs or biological agents. The compounds also may be administered in conjunction with the administration of other drugs or biological agents useful for the disease or condition that the invention compounds are directed (see e.g., U.S. Pat. No. 6,413,955 for active ingredients useful for osteoporosis).

Compounds comprising a polynucleotide including a sequence encoding an inflammatory response control element or fragment thereof of the present invention may also be introduced into tissues or cells by a "gene gun." DNA may be coated onto gold microparticles, and delivered intradermally by a particle bombardment device, or "gene gun" as described in the literature (see, for example, Tang et al. (1992), Nature 356:152-154), where gold microprojectiles are coated with the therapeutic DNA, then bombarded into skin cells.

As employed herein, the phrase "an effective amount" refers to a dose sufficient to provide concentrations high enough to impart a beneficial effect on the recipient thereof. The specific therapeutically effective dose level for any particular subject will depend upon a variety of factors including the disorder being treated, the severity of the disorder, the activity of the specific compound, the route of administration, the rate of clearance of the compound, the duration of treatment, the drugs used in combination or coincident with the compound, the age, body weight, sex, diet and general health of the subject, and like factors well known in the medical arts and sciences. Various general considerations taken into account in determining the "therapeutically effective amount" are known to those of skill in the art and are described, e.g., in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990.

Adjuvants

For delivery of a polynucleotide including a sequence encoding an inflammatory response control element or fragment thereof to a mammalian system, it is usually preferable to utilize a delivery system. Such a system can provide multiple benefits, notably providing stabilization to protect the integrity of the DNA, as well as assisting in cellular uptake.

In addition, as illustrated by an exemplary delivery system described herein, the non-DNA components of the formulation can contribute to an immune system enhancement or activation. As a result, components of a delivery system can be selected in conjunction with a particular gene product to enhance or minimize the immuno-stimulatory effect.

Immunostimulatory effects are also described for certain nucleotide sequences. For example, Sato et al., Science 273: 352-354 (1996) describes the effects of vaccination with dsDNA having certain CpG containing sequences on the production of interferon-γ; interferon-β, and interleukin-12.

Transfection Reagents

Compositions comprising a polynucleotide including a sequence encoding an inflammatory response control element or fragment thereof of the invention can also include one or more transfection facilitating materials that facilitate delivery of polynucleotides to the interior of a cell, and/or to a desired location within a cell. Many such transfection facilitating materials are commercially available, for example Lipofectin, Lipofectamine, Lipofectamine 2000, Optifect, SuperFect. Examples of transfection facilitating materials include, but are not limited to lipids, preferably cationic lipids; inorganic materials such as calcium phosphate, and metal (e.g., gold or tungsten) particles (e.g., "powder" type delivery solutions); peptides, including cationic peptides, targeting peptides for selective delivery to certain cells or intracellular organelles such as the nucleus or nucleolus, and amphipathic peptides, i.e. helix forming or pore forming peptides; basic proteins, such as histones; asialoproteins; viral proteins (e.g., Sendai virus coat protein); pore-forming proteins; and polymers, including dendrimers, star-polymers, "homogenous" poly-amino acids (e.g., poly-lysine, poly-arginine), "heterogenous" poly-amino acids (e.g., mixtures of lysine & glycine), co-polymers, polyvinylpyrrolidinone (PVP), and polyethylene glycol (PEG). Furthermore, those auxiliary agents of the present invention which facilitate and enhance the entry of a polynucleotide into vertebrate cells in vivo, may also be considered "transfection facilitating materials."

Lipofection facilitated transfection is well known in the art as described, for example, in U.S. Pat. Nos. 6,034,072, 6,040, 295 and 6,710,035. Certain embodiments of the present invention may include lipids as a transfection facilitating material, including cationic lipids (e.g., DOTMA, DMRIE, DOSPA, DC-Chol, GAP-DLRIE), basic lipids (e.g., steryl amine), neutral lipids (e.g., cholesterol), anionic lipids (e.g., phosphatidyl serine), and zwitterionic lipids (e.g., DOPE, DOPC). Preferably, the cationic lipid is mixed with one or more co-lipids. For purposes of definition, the term "co-lipid" refers to any hydrophobic material which may be combined with the cationic lipid component and includes amphipathic lipids, such as phospholipids, and neutral lipids, such as cholesterol. Cationic lipids and co-lipids may be mixed or combined in a number of ways to produce a variety of non-covalently bonded macroscopic structures, including, for example, liposomes, multilamellar vesicles, unilamellar vesicles, micelles, and simple films.

Delivery can also be through use of DNA transporters. DNA transporters refers to molecules which bind to DNA vectors and are capable of being taken up by epidermal cells. DNA transporters contain a molecular complex capable of noncovalently binding to DNA and efficiently transporting the DNA through the cell membrane. A DNA transporter system can consist of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine. A first element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide.

Animal Models

β-tubulin is one of the predominant proteins to which autoimmune responses are generated in Meniere's disease. In order to understand the MD autoimmune disease effectively, animal models were developed to understand the immunological mechanisms leading to the manifestation of the disease process. β-tubulin is a major intracellular protein in microtubules, prominent in structures in the sensory and supporting cells of the organ of Corti in the inner ear β-tubulin is believed to be responsible for movement of subcellular organelles (Araki, N., et al., Experimental Cell research, vol. 204(2), p. 181-91 (1993)), establishment of cell polarity (Hyde, G. J., et al., Eur. J. Cell Biol., vol. 62, p. 75-85 (1993)), maintenance of cell shape (Bulinski, J. C., et al., Bio. Essays, vol. 13, p. 285-93 (1991)), and the provision of structural support (Deanin, G. G., et al., Biochem. Biophys. Res. Commun., vol. 1, p. 1642-50 (1981)). The determination of cell polarity and shape and the permanence of structures containing microtubules are related to their dynamic properties (Schulze, E., et al., J. Cell Biol., vol. 104, p. 277-88 (1987)). Dynamic properties may be determined by the biochemical composition of tubulin (Tannenbaum, J., et al., vol. 38, p. 146-162 (1997) and Gunderson, G. G., et al., J. Cell Biol., vol. 105, p. 251-64 (1987)). Furthermore, immunohistological studies of guinea pig organ of Corti using monoclonal anti-tubulin antibody showed that it is stained in the hair cells, the supporting cells, the spiral limbs, and the neural pathways of the cochlea nerve as well as the spiral ganglions (Yoo, T. J., Tanaka, H., et al. Meniere's Disease update, p. 529-535 (1999)).

Elevated β-tubulin antibody has been observed in sera of patients suffering from a variety of autoimmune disorders such as chronic demyelinating polyneuropathy syndrome (Connolly, A. M., et al., Neurology, vol. 48, p. 243-48 (1997)), Guillian-Barre syndrome (Manfredini, E., et al., J. Neuro. Sci., vol. 133, p. 79-84 (1995)), amyotropic lateral sclerosis (Kurisaki, H., et al., J. Rinsho-shin Keigakee Clin. Neuro., vol. 23, p. 1013-20 (1983)), recent onset type 1 diabetes mellitus (Rousset, B., Vialettes, B., et al., Clin. Exp. Immunol., vol. 52, p. 325-32 (1984)), and autoimmune thyroid disorders like Grave's disease and Hashimoto's thyroiditis membrane with amino acid sequences of β-tubulin (Yoo, T. J., Tanaka, H., et al.). A study of sera from 113 patients with Meniere's disease showed that 59% of the patients had antibody against tubulin implying that autoimmunity to the tubulin molecule in some patients with Meniere's disease. Thus, β-tubulin is capable of inducing autoimmune hearing loss, in particular, in mice upon immunization. Understanding the mode of action of autoimmunity helps prevent or reduce severity of autoimmunity by including a tolerance to the particular antigen such as β-tubulin. The β-tubulin animal model in mice is used to test various immunological strategies. In general, Th1 type cytokines, such as IFN-γ and IL-2, perpetuate the inflammatory response in the lesions of autoimmunity, whereas Th2 type cytokines, such as IL-4, IL-10, represent one way in which the inflammatory response may be controlled. In addition to cytokines, new genes expressed in CD4+ T cells during the induction of immunological unresponsiveness, called "anergy," have been identified.

EXAMPLE 1

β-Tubulin Animal Model Study

Four week old female BALB/c mice weighing between 18-20 grams (Jackson Laboratory, Bar Harbor, Me.) are used to monitor auditory responses. Initially, the mice have normal bilateral auditory behavior in auditory brainstem responses (ABR), generated by neurological responses, and distortion product of otoacoustic emission (DPOAE), generated by cochlear stimulation, as well as normal startle reflex and tympanic membranes. Mice in the immunization group are subcutaneously injected at the base of the tail with purified β-tubulin in dosages ranging from 100 μg, 200 μg and 300 μg. Mice in the control group are subcutaneously injected with 0.10 M sterile phosphate buffer saline (PBS) and complete Freund's adjuvant (CFA). Immunizations are boosted in incomplete Freund's adjuvant (IFA) with 100 μg, 200 μg and 300 μg purified β-tubulin per group twice at one-week internals, two weeks after the initial immunization. Control mice are given PBS in IFA at contemporaneous booster times. Results from animal model experimentation provide proof-of-principle of adoptive cellular gene therapy in other organisms, particularly humans.

EXAMPLE 2

Figure 2:
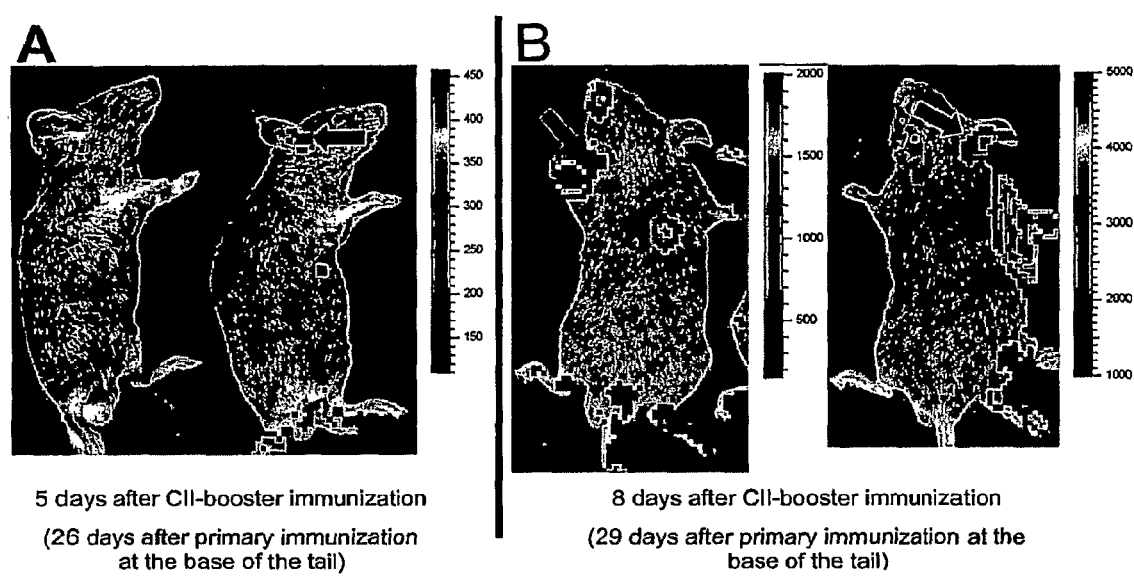
FIG. 2. Experiment showing homing ability of Type II collagen specific T cell hybridomas to sites of CII-induced inflammation in DBA/1LacJ mice.
Figure 3A:
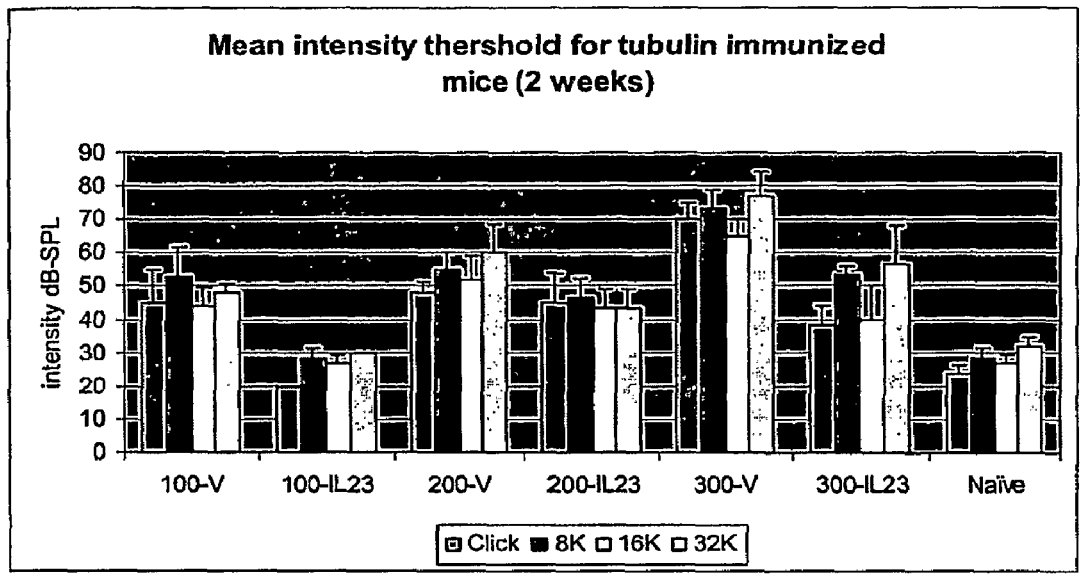
FIG. 3. Mean intensity thresholds of β-tubulin immunized mice at 2 (FIG. 3A) and 6 weeks (FIG. 3B) after final booster. ABR levels are provided for 1) vector control mice (100-V, 200-V, and 300-V); 2) IL-12p40 therapeutic group mice (100-IL23, 200-IL23, and 300-IL23); and naïve mice. Described in Example 3.
Figure 3B:
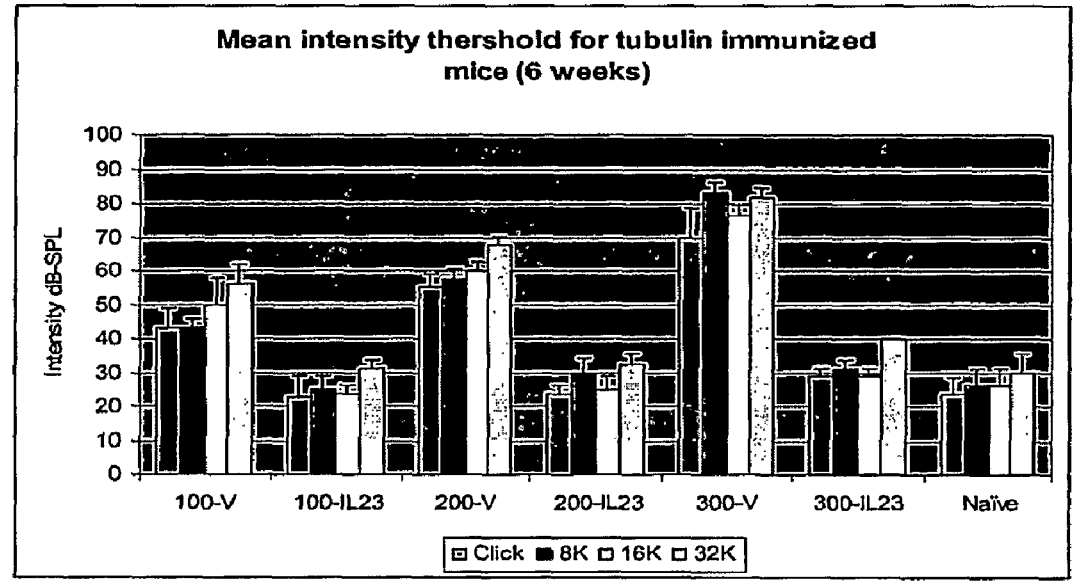

Homing Ability of CII-Specific T Cell Hybridomas to Sites of CII-Induced Inflammation CII-specific (collagen type II) CD4+ T cell hybridomas retrovirally transduced to express the enzyme luciferase are injected intravenously to adoptively transfer $1 \times 10^6$ cells (plasmid gene Coste-GFP-Luc vector construct) are visualized in vivo in real time using bioluminescence imaging. Upon intraperitoneal (i.p.) injection of the substrate luciferin into anesthetized mice, photons are emitted from sites in which luciferase-expressing hybridomas cells catalyze the ATP- and $O_2$-dependent conversion of luciferin to oxyluciferin. Emitted photons can travel through biological tissue and are detected using a sensitive cooled charge-coupled device camera. Using this system, mice injected with T cell hybridomas luminesced at the site of CII-immunization at the base of the tail, the mildly inflamed areas such as the paws and ears. Subsequent observations of the same mice continued to bioluminescence at sites of inflammation. Shown in FIG. 2.

EXAMPLE 3

Delivery of Cell Free Products to Inflammatory Autoimmune Disease Sites

Autoantigen-specific CD4+ T cells can transfer organ-specific autoimmune disease in mice and humans. CD4+ T cells can be found in target organs of both human and mouse models of autoimmunity, thus providing tissue-specific homing properties. Because of this, CD4+ T cells retrovirally transduced to express regulatory proteins are ideal for local delivery of therapeutic gene products. Expression of immune-regulatory proteins by adoptively transferred autoantigen-specific CD4+ T cells could ameliorate the clinical signs of experimental autoimmune encephalomyelitis (EAE) (Cheng, K. C., et al.; Matsuoka, H., et al. and Yoo, T. J., Tanaka, H., et al.) and collagen induced arthritis (CIA) (Tamer, I. H., et al.; Nakajima, A., et al.; and Tuohy, V. K., et al.). These reports provide indirect evidence that homing to sites of inflammation is necessary for therapeutic effects. Development of the Th1 subset during an immune response is influenced by the cytokines present during the initial phase of the immune response, where a bioactive cytokine, IL-12, plays a major role. IL-12 is a heterodimeric protein composed of 35-kDA (p35) and 4-kDA (p40) subunits, for which the latter is responsible for receptor binding (Nakajima, A., Serology, C. M., et al., J. Clin. Invest., vol. 107, p. 1293-1301 (2001)). It has been demonstrated that the expression of p35 and p40 is differentially regulated and that IL-12p40 can be produced as a homodimer or a monomer in the absence of p35, and act as an IL-12 receptor agonist in vitro and in vivo (Mattner, F., et al., Eur. J. Immunol., vol. 23, p. 2202-08 (1993); Segal, B. M., et al., J. Exp. Med., vol. 187, p. 537-46 (1998); and Ling, P., et al., J. Immunol., vol. 154, p. 116-27 (1995). It was also shown that development of Th1-mediated autoimmune CIA can be inhibited by local expression IL-12p40 (Nakajima, A., Seroogy, C. M., and Costa, G. L., Sandora, M. R., J. Immunol., vol. 167(4), p. 2379-87 (2001)).

Studies of constitutive delivery of IL-12p40 by retrovirally transduced CII-specific T cell hybridomas show amelioration of tubule induced hearing loss (TIAHL). The therapeutic effect is the result of expression of the immune-regulatory protein in the inflamed ear tissues, not in the regional lymph nodes. The study further provides that local delivery of therapeutic proteins via antigen specific T cells can control autoimmune inner ear disease (AIED) locally at the site of inflammation.

Local delivery of an inflammatory response control protein such as IL-12p40 can be achieved using antigen specific (tissue specific) T cells as a delivery vehicle for TIAHL. Amelioration of AIED would be due to local delivery and retention of IL-12p40, expressing cells in the inflamed ear tissue. The development of TIAHL can be inhibited by local suppression of Th1-type autoimmune responses in the ear tissues by means of T cell hybridoma-mediated adoptive cellular gene therapy. It has been determined that autoantigen-specific CD4+ T cells and T cell hybridomas migrate into inflamed autoantigen-expressing tissues in the TIAHL model. Using retrovirally transduced CII-specific CD4+ T lymphocytes as a vehicle for delivery of IL-12p40. Thus, TIAHL can be efficiently controlled by this form of adoptive cellular gene therapy.

β-tubulin induced hearing loss mice are infused with $2\times10^6$ CD4+ hybridomas cells transduced with the IL-12p40 gene. Control mice are injected as described above. ABR and DPOAE of mice are initially measured prior to immunization. At week 1, mice receive an initial immunization. At week 3 and 4, booster injections are provided to both groups of mice. Prior to immunization and at weeks 2, 6 and 10, ABR and DPOAE are measured. At week 12, the mice are sacrificed.

The intensity threshold for β-tubulin for mice immunized with 100 μg IL-12p40 already showed a marked increase in comparison with the control group at week 2. At week 6, most of the mice that received gene therapy improved their hearing. The intensity of decibel-sound pressure levels (dB-SPL) were similar to naïve mice that did not receive any autoantigen immunization. These results show that adoptive gene therapy with CD4+ hybridomas cells transduced with the IL-12p40 gene restored hearing levels over 90%.

Figure 4A:
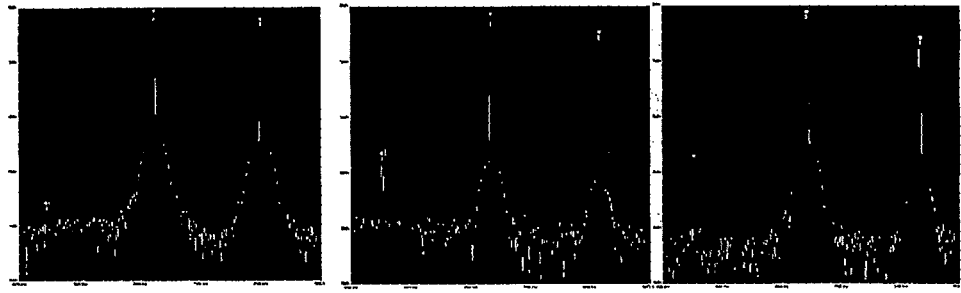
FIG. 4. DPOAE distortion traces of β-tubulin immunized mice treated. DPOAE measurements are provided for 1) vector control mice (left); 2) IL-12p40 therapeutic group mice (middle); and naïve mice (right). Described in Example 3.
Figure 4B:
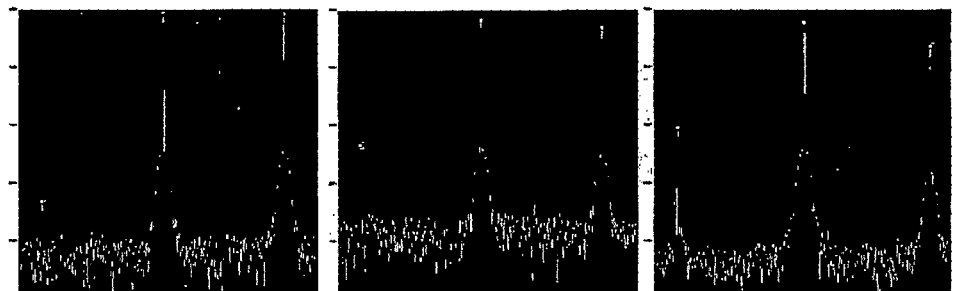
Figure 4C:
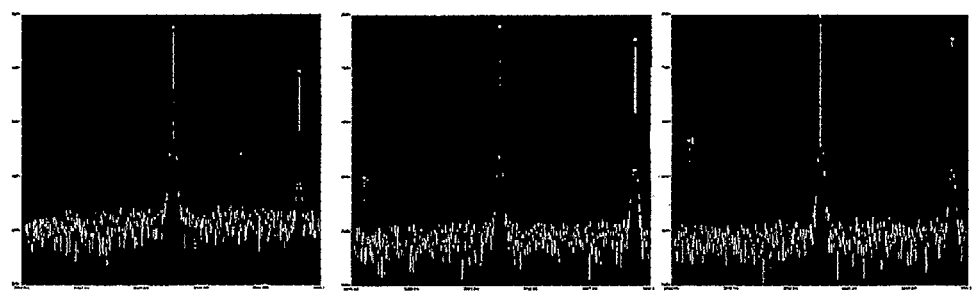
Figure 5:
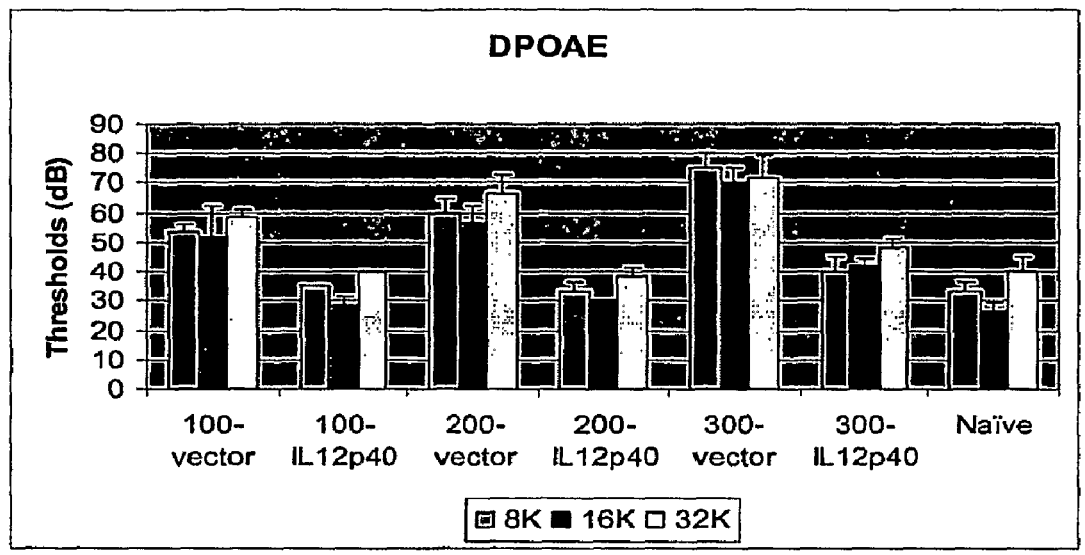
FIG. 5. Distortion product traces at 32 KHz in β-tubulin immunized mice. DPOAE measurements are provided for 1) vector control mice (100-V, 200-V, and 300-V); 2) IL-12p40 therapeutic group mice (100-IL12p40, 200-IL12p40, and 300-IL12p40); and naïve mice.
Figure 6:
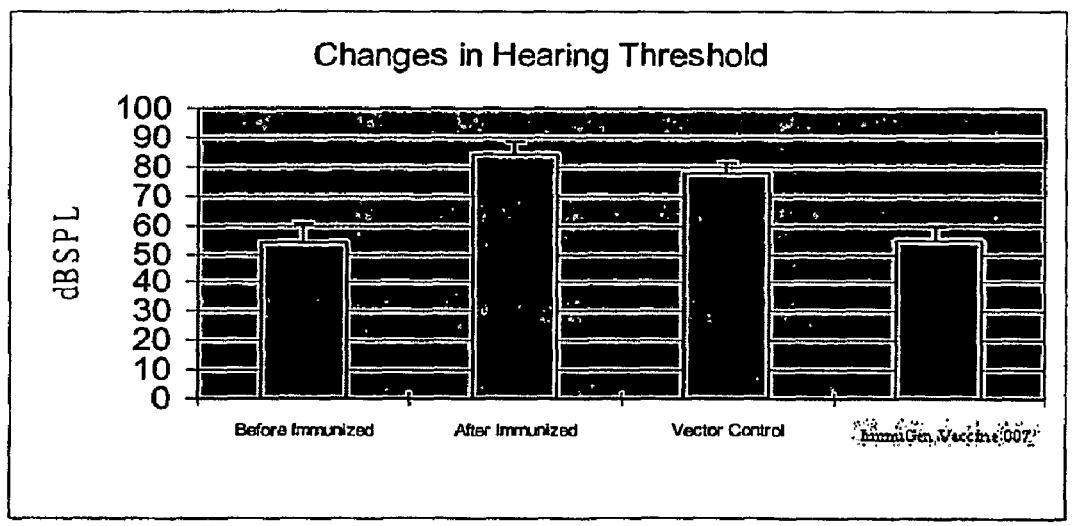
FIG. 6. Distortion product traces of changes in hearing threshold throughout treatment with IL-10 DNA vaccine (ImmuGen Vaccine 007).
Figure 7:
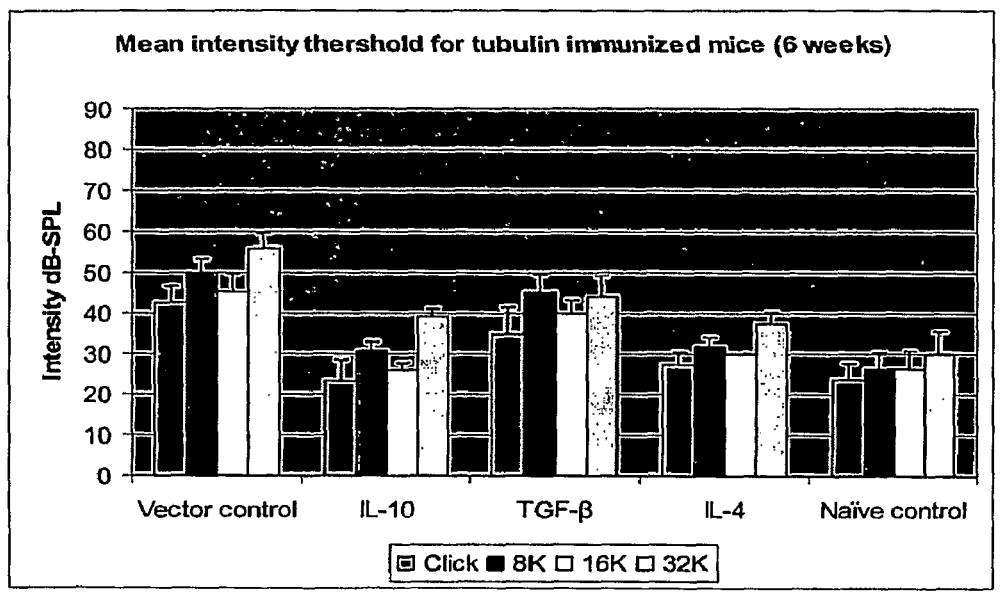
FIG. 7. Mean intensity threshold for β-tubulin induced hearing loss in mice with DNA vaccine treatment with IL-4, IL-10 and TGFβ.
Figure 8:
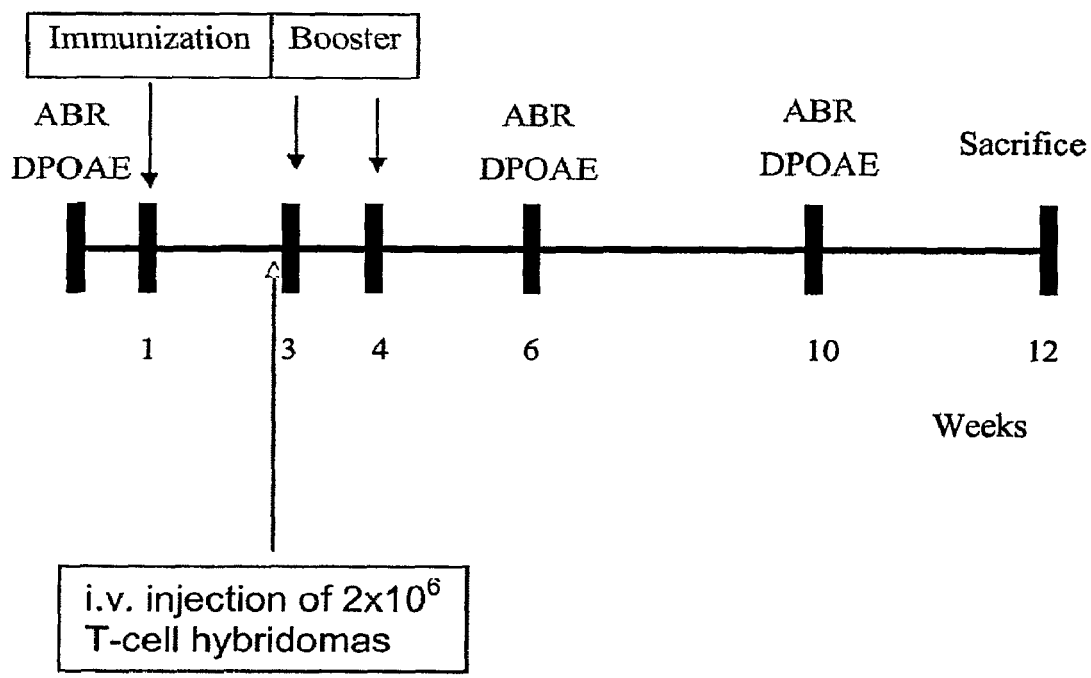
FIG. 8. Sample treatment schedule in mice experiments.
Figure 9:
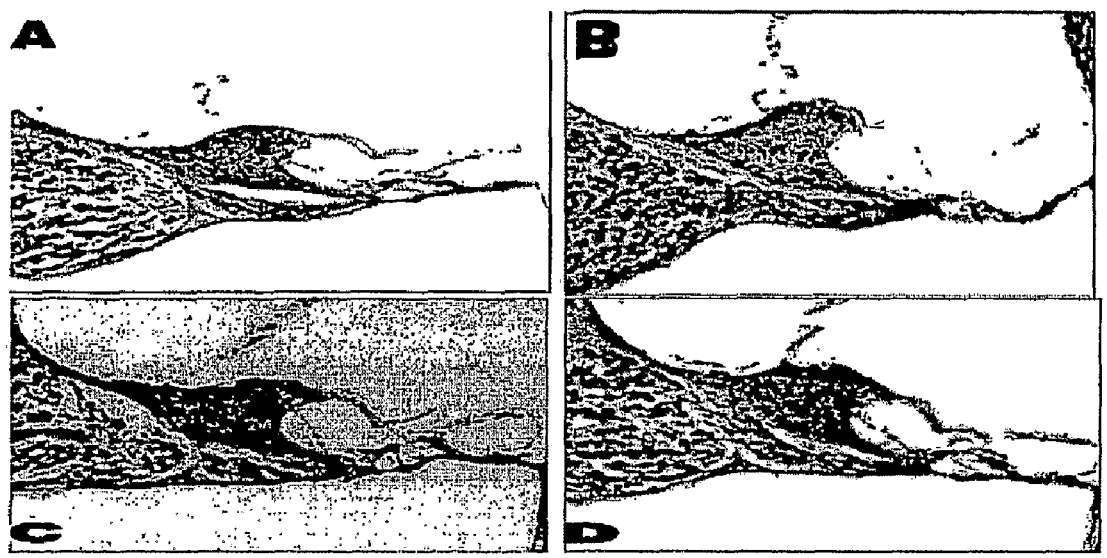
FIG. 9. Organ of Corti images. A. Control. B. Shows loss of hair cells after administration of β-tubulin. C and D. Organ of Corti are intact after treatment of T cell gene therapy with IL-12p40.
Figure 10:
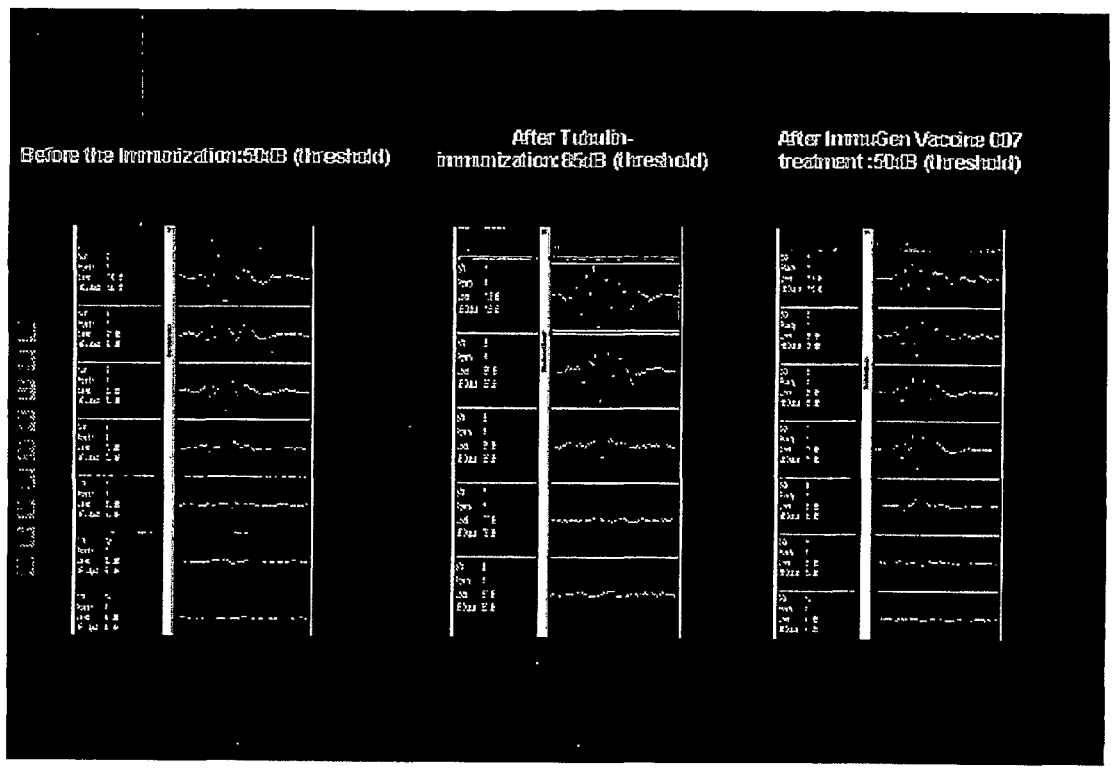
FIG. 10. DPOAE profiles of IL-10 gene therapy in β-tubulin induced hearing loss in guinea pigs which show that the IL-10 DNA vaccine partly restored hearing.

Cochlea electric response is also measured in mice by measuring DPOAE. Three groups of mice were tested. The first group was immunized with 300 μg of β-tubulin (immunized group), the second group was immunized with 300 μg of β-tubulin followed by injection of transduced T cells (therapeutic group), and the third group did not receive any injection (control group). The immunized group had little or no response to cochlear stimulation and the treatment group had restored hearing levels as good as or better than the control group at 8 KHz frequency fl=7278 Hz, f2=8722 Hz and DP=5834 Hz at 8 dB SPL intensity; 16 KHz frequency fl=1364 Hz, f2=16346 Hz and DP=1934 Hz at 8 dB SPL intensity; and 32 KHz frequency fl=2989 Hz, f2=34888 Hz and DP=2329 Hz at 8 dB SPL intensity. At week 6, the immunized group showed no response to DPOAE while the therapeutic group had restored hearing levels. In addition, at week 6, all of the subjects in the therapeutic group treated with the IL-12p40 gene had restored hearing. As shown in FIGS. 4A, 4B and 4C.

In summary, the ABR and DPOAE results at week 2 of adoptive cellular therapy show that the mean intensity threshold for β-tubulin immunized mice has a marked improvement in hearing for the treatment groups administered with 100 μg, 200 μg and 300 μg of IL-12p40 as compared with the immunized group. At week 6, most of the mice given the different dosages of IL-12p40 had improved hearing levels comparable to that of naïve mice that had never received any autoantigen immunization with β-tubulin.

The Organ of Corti of the treatment and control groups was also observed. After administration of β-tubulin, hair loss resulted at the Organ of Corti. Subsequent to treatment with IL-12p40, in addition to restoration of hearing, hair recovery resulted as well.

EXAMPLE 4

Restoring Hearing Loss Using a DNA Vaccine

Guinea pigs and mice were tested for restoration of hearing loss using DNA vaccines encoding an inflammatory response control gene such as IL-10, IL-4 or TGF-β or a portion of the gene. Hearing loss was restored in both guinea pigs and mice. β-tubulin was again used to induce hearing loss in the test animals. In one experiment, mice were injected with 50 μg of plasmid DNA intramuscularly three times at weekly intervals. The plasmid DNA was emulsified with an equal volume of complete Freund's adjuvant (CFA) for immunization. The first group was vaccinated with blank vector PBS (control mice) and the second group was vaccinated with plasmid encoding a an inflammatory response control gene construct in PBS (treatment group mice). Administration of plasmid DNA with genes encoding an inflammatory response gene restored hearing loss to levels comparable to naïve mice that were never exposed to autoantigens.

EXAMPLE 5

Restoring Hearing Loss Using Dendrite or Stem Cells

A. Retrovirus Construction, Transfection and Infection

Three cells lines of CII-specific T cell hybridomas are prepared, expressing IL-12p40, IL-4 or anti TNF-scFv. Transient transfection of a Phoenix-ECO producer line with plasmid pGCy only (derived from the previously described Moloney murine leukemia virus-based retroviral vector (Costa, G. L., et al., J. Immunol, vol. 164, p. 3581-90 (2000))) or pGCy combined with IL-12p40 (named pGCy.IL-12p40) are performed and viral supernatants are used to transduce the T cell hybridomas by "spin infection." $2–5\times10^6$ cells per well in 6-well plates (BD Falcon, Franklin Lakes, N.J.) are overlaid with 2 ml thawed recombinant retroviral supernatant (pGCy or pGCy.IL-12p40) supplemented with protamine sulfate (8 μg/ml; Sigma, St. Louis, Mo.). The samples are centrifuged at 25 rpm, 32° C. for 2 hours and then incubate at 32° C. in 6% $CO_2$ overnight. At 48 hours after infection, cells are analyzed for transduction and sorted by FACS (FACStar cell sorter, Becton Dickinson Immunocytometry Systems, San Jose, Calif.) based on either GFP- or YFP-fluorescence and on TCR Vβ8.2 expression, using anti TCR Vβ8.2 (MR5-2) antibody (BD Pharmingen, San Diego, Calif.). The FACS data is analyzed using FlowJo software (Treestar, San Carlos, Calif.).

B. Lentivirus Production

Seed 1-12 T175 flasks with 293T cells and 25 ml medium (c-IMDM) per flask ($15\times10^6$ cells per flask). After 24 hours, the cells should be 8-9% confluent. Replace medium with 25 ml fresh c-IMDM containing 25 μM chloroquine. In a 5 ml tube add: sterile purified water containing pHR vector, pt, pVSVG, $CaCl_2$, and HBS mix. Immediately add the mixture dropwise to the T175 flask. Incubate at 37° C. for 8 hours. Replace the transfection medium with 2 ml fresh c-IMDM medium per flask. Incubate at 37° C. overnight. On the morning of the third day, remove the supernatant and pool into 5 ml tubes. Spin the tubes for 1 min. at 2 rpm. Filter the supernatant with 0.45 μm unit filters. Split the supernatant into an Ultra-Clear tube (Beckman Instruments, Fullerton, Calif.). Centrifuge in a SW28 rotor for 14 min. at 195 rpm at 4° C. (minimum brake). After centrifugation, immediately discard supernatant. Resuspend each pellet to concentrate 1-2× (e.g., 1-2 μl serum-free IMDM). Aliquot and freeze the resuspension at −8° C. Viral titers are determined by infection of 293T cells with serial dilutions of the vector stock. 72 hours after infection, the number of (enhanced green fluorescence protein) eGFP-positive cells can be scored by flow cytometry to determine the titer. T cell hybridomas are lentivirally transduced in 48 well plates by resuspending $1\times10^6$ cells in 2 μl of complete RPMI-F medium concentrated virus supernatant at a multiplicity of infection (MOI) of 15 with 8 μg/ml protamine sulphate. After incubation at 37° C. with 5% $CO_2$ for 2 hours, the volume is filled to 1 ml/well and cells are transferred into a 24-well plate. After incubation for 24 hours, cells are transferred into 25 $cm^2$ tissue culture flasks and expanded as needed. Transduction efficiency is assessed by flow cytometry analysis of eGFP expression. Transduced cells are sorted by FACS and expanded as needed before adoptive transfer into animals. For adoptive transfer, cells are harvested by centrifugation and washed three times in 0.9% NaCl solution and finally resuspended at $1\times10^6$ cells/ml in 0.9% NaCl solution. A volume of 1 µl of cell suspension, corresponding to $1\times10^6$ cells, is injected intravenously (i.v.) into the tail vein using a 1 ml tuberculin syringe and a 27¾ G needle.

C. β-Tubulin Induced Hearing Loss

TIAHL is induced as follows. BALB/c mice are immunized intradermally (i.d.) at the tail base with 300 µg of β-tubulin emulsified with an equal volume of CFA containing 1 µg of H37Ra *Mycobacterium tuberculosis* (Difco, Detroit, Mich.). On day 21, mice are boosted by intradermal (i.d.) injection with 3 µg of β-tubulin emulsified with IFA at the base of the tail. Starting on the day before the booster immunization (day 2), groups of BALB/c mice receive i.v. or i.p. injections of $2\times10^6$ cells of pGCy.IL-12p40 transduced CII-specific T cell hybridomas or $5\times10^6$ cells of transduced CII-specific primary T cells. For treatment experiments, adoptive cell transfer is performed on the day of the first clinical signs of TIAHL. pGCy-transduced CII-specific T cell hybridomas are used as controls for both prevention and treatment experiments.

D. Transfection Assay

A total of $2\times10^6$ dendrite cells, stem cells or 3T3 fibroblast cells are cultured in 12 ml DMEM-C medium in 1 mm tissue culture dishes (Nalge Nunc International, Roskilde, Denmark). Following overnight incubation, cells are transfected with 1 µg of retroviral plasmid DNA (Qiagen, Valencia, Calif.) or no plasmid DNA (control) using a modified version of the calcium phosphate precipitation protocol. At 8-12 hours after transfection, calcium phosphate containing medium replaces the DMEM-C medium and cultures are maintained at 37° C. in 6% $CO_2$ for 24-48 hours and then at 32° C. in 6% $CO_2$ for 16-24 hours. Viral supernatant from transfected cultures are harvested and filtered using a 0.45 µm filter (Nalge Nunc International) and then store at 8° C. Virus titers are determined using 3T3 lines as previously described and virus stocks with titers>$4\times10_6$ are used. Nucleofector technology (Amaxa Biosystems, Gaithersburg, Md.) can also be used for transfection experiments.

Animals treated in these experiments had lower incidence of ear lesions (due to prevention) and/or lower severity of ear lesions (due to amelioration). Thus dendrite cells, stem cells and 3T3 cells transduced to express various inflammatory response control genes such as IL-12p40, IL-4 and TNFα-scFv home to ear tissue and ameliorate or prevent the hearing loss by local delivery of the response control genes.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

That which is claimed is:

1. A method of treating or ameliorating hearing loss, said method comprising administering a composition comprising nucleic acid that reduces inflammation, wherein said nucleic acid comprises a sequence encoding IL-10.

2. The method of claim 1, wherein said nucleic acid comprises one or more selected from the group consisting of a polynucleotide, DNA, RNA.

3. The method of claim 1, wherein said polynucleotide is a plasmid comprising a promoter/enhancer transcriptionally linked to said sequence encoding an inflammatory response control polypeptide.

4. The method of claim 1, wherein said nucleic acid is administered with a transfection facilitating material.

5. The method of claim 1, wherein said administering comprises one or more methods selected from the group consisting of intravenous injection, intramuscular injection, intraperitoneal injection, subcutaneous injection, inhalation, and gene gun.

6. The method of claim 1, wherein said hearing loss is caused by an autoimmune disease.

7. The method of claim 6, wherein said autoimmune disease is an autoimmune inner ear disease.

8. The method of claim 7, wherein said autoimmune inner ear disease is Menier's disease.

9. The method of claim 1, wherein said administering increases expression of a gene that decreases inflammation.

10. The method of claim 1, wherein said nucleic acid further comprises one or more sequences selected from SEQ ID NOs: 1-15.

* * * * *

SEQUENCE LISTING

```
<160> NUMBER OF SEQ ID NOS: 32

<210> SEQ ID NO 1
<211> LENGTH: 614
<212> TYPE: DNA
<213> ORGANISM: Homo sapiens

<400> SEQUENCE: 1
gatcgttagc ttctcctgat aaactaattg cctcacattg tcactgcaaa tcgacaccta      60
ttaatgggtc tcacctccca actgcttccc cctctgttct tcctgctagc atgtgccggc     120
aactttgtcc acggacacaa gtgcgatatc accttacagg agatcatcaa aactttgaac     180
agcctcacag agcagaagac tctgtgcacc gagttgaccg taacagacat ctttgctgcc     240
```

```
tccaagaaca caactgagaa ggaaaccttc tgcagggctg cgactgtgct ccggcagttc    300
tacagccacc atgagaagga cactcgctgc ctgggtgcga ctgcacagca gttccacagg    360
cacaagcagc tgatccgatt cctgaaacgg ctcgacagga acctctgggg cctggcgggc    420
ttgaattcct gtcctgtgaa ggaagccaac cagagtacgt ggaaaacttc ttggaaagg     480 ctaaagacga tcatgagaga gaaatattca agtgttcga gctgaatatt ttaatttatg     540 agttttgat agctttattt tttaagtatt tatatattta aactcatca taaaataaag      600 tatatataga atct                                                      614

<210> SEQ ID NO 2
<211> LENGTH: 459
<212> TYPE: DNA
<213> ORGANISM: Homo sapiens

<400> SEQUENCE: 2
caaacgcaga acgtttcaga gccatgagga tgcttctgca tttgagtttg ctagctcttg     60
gagctgccta cgtgtatgcc atccccacag aaattcccac aagtgcattg gtgaaagaga    120
ccttggcact gctttctact catcgaactc tgctgatagc caatgagact ctgaggattc    180
ctgttcctgt acataaaaat caccaactgt gcactgaaga aatctttcag ggaataggca    240
cactggagag tcaaactgtg caaggggta ctgtggaaag actattcaaa aacttgtcct     300
taataaagaa atacattgac ggccaaaaaa aaagtgtgg agaagaaaga cggagagtaa     360
accaattcct agactacctg caagagtttc ttggtgtaat gaacaccgag tggataatag    420
aaagttgaga ctaaactggt tgttgcagcc aaagataac                           459

<210> SEQ ID NO 3
<211> LENGTH: 1601
<212> TYPE: DNA
<213> ORGANISM: Homo sapiens

<400> SEQUENCE: 3
aaaccacaag acagacttgc aaaagaaggc atgcacagct cagcactgct ctgttgcctg     60
gtcctcctga ctggggtgag ggccagccca ggccagggca cccagtctga aacagctgc     120 acccacttcc caggcaacct gcctaacatg cttcgagatc tccgagatgc cttcagcaga    180
gtgaagactt tctttcaaat gaaggatcag ctggacaact tgttgttaaa ggagtccttg    240
ctggaggact ttaagggtta cctgggttgc caagccttgt ctgagatgat ccagttttac    300
ctggaggagg tgatgcccca agctgagaac caagacccag acatcaaggc gcatgtgaac    360
tccctggggg agaacctgaa gaccctcagg ctgaggctac ggcgctgtca tcgatttctt    420
ccctgtgaaa acaagagcaa ggccgtggag caggtgaaga atgccttaa taagctccaa    480 gagaaaggca tctacaaagc catgagtgag tttgacatct tcatcaacta catagaagcc    540
tacatgacaa tgaagatacg aaactgagac atcagggtgg cgactctata gactctagga    600
cataaattag aggtctccaa aatcggatct ggggctctgg gatagctgac ccagccccett   660 gagaaacctt attgtacctc tcttatagaa tatttattac ctctgatacc tcaaccccca    720
tttctattta tttactgagc ttctctgtga acgatttaga aagaagccca atattataat    780 tttttcaat atttattatt ttcacctgtt tttaagctgt ttccataggg tgacacacta    840
tggtatttga gtgttttaag ataaattata agttacataa gggaggaaaa aaaatgttct    900
ttggggagcc aacagaagct tccattccaa gcctgaccac gctttctagc tgttgagctg    960
ttttccctga cctccctcta atttatcttg tctctgggct tggggcttcc taactgctac   1020
```

```
aaatactctt aggaagagaa accagggagc cccttttgatg attaattcac cttccagtgt    1080
ctcggaggga ttccccctaac ctcattcccc aaccacttca ttcttgaaag ctgtggccag    1140 cttgttatttt ataacaacct aaatttggtt ctaggccggg cgcggtggct cacgcctgta    1200
atcccagcac tttgggaggc tgaggcgggt ggatcacttg aggtcaggag ttcctaacca    1260
gcctggtcaa catggtgaaa ccccgtctct actaaaaata caaaaattag ccgggcatgg    1320
tggcgcgcac ctgtaatccc agctacttgg gaggctgagg caagagaatt gcttgaaccc    1380
aggagatgga agttgcagtg agctgatatc atgcccctgt actccagcct gggtgacaga    1440
gcaagactct gtctcaaaaa aataaaaata aaaataaatt tggttctaat agaactcagt    1500
tttaactaga atttattcaa ttcctctggg aatgttacat tgtttgtctg tcttcatagc    1560
agattttaat tttgaataaa taaatgtatc ttattcacat c                        1601

<210> SEQ ID NO 4
<211> LENGTH: 1282
<212> TYPE: DNA
<213> ORGANISM: Homo sapiens

<400> SEQUENCE: 4
aagccaccca gcctatgcat ccgctcctca atcctctcct gttggcactg ggcctcatgg      60
cgcttttgtt gaccacggtc attgctctca cttgccttgg cggctttgcc tccccaggcc     120
ctgtgcctcc ctctacagcc ctcagggagc tcattgagga gctggtcaac atcacccaga     180
accagaaggc tccgctctgc aatggcagca tggtatggag catcaacctg acagctggca     240
tgtactgtgc agccctggaa tccctgatca acgtgtcagg ctgcagtgcc atcgagaaga     300
cccagaggat gctgagcgga ttctgcccgc acaaggtctc agctgggcag ttttccagct     360
tgcatgtccg agacaccaaa atcgaggtgg cccagtttgt aaaggacctg ctcttacatt     420
taaagaaact ttttcgcgag ggacagttca actgaaactt cgaaagcatc attatttgca     480
gagacaggac ctgactattg aagttgcaga ttcatttttc tttctgatgt caaaaatgtc     540
ttgggtaggc gggaaggagg gttagggagg ggtaaaattc cttagcttag acctcagcct     600
gtgctgcccg tcttcagcct agccgacctc agccttcccc ttgcccaggg ctcagcctgg     660
tgggcctcct ctgtccaggg ccctgagctc ggtggaccca gggatgacat gtccctacac     720
ccctcccctg ccctagagca cactgtagca ttacagtggg tgccccctt gccagacatg     780 tggtgggaca gggacccact tcacacacag gcaactgagg cagacagcag ctcaggcaca     840
cttcttcttg gtcttattta ttattgtgtg ttatttaaat gagtgtgttt gtcaccgttg     900
gggattgggg aagactgtgg ctgctagcac ttggagccaa gggttcagag actcaggcc      960 ccagcactaa agcagtggac accaggagtc cctggtaata agtactgtgt acagaattct    1020
gctacctcac tgggtcctg gggctcgga gcctcatccg aggcagggtc aggagagggg    1080
cagaacagcc gctcctgtct gccagccagc agccagctct cagccaacga gtaatttatt    1140 gttttttcctt gtatttaaat attaaatatg ttagcaaaga gttaatatat agaagggtac    1200
cttgaacact gggggagggg acattgaaca agttgtttca ttgactatca aactgaagcc    1260
agaaataaag ttggtgacag at                                              1282

<210> SEQ ID NO 5
<211> LENGTH: 1007
<212> TYPE: DNA
<213> ORGANISM: Homo sapiens
```

-continued

```
<400> SEQUENCE: 5
agcaagatgt gtcaccagca gttggtcatc tcttggtttt ccctggtttt tctggcatct      60
cccctcgtgg ccatatggga actgaagaaa gatgtttatg tcgtagaatt ggattggtat     120
ccggatgccc ctggagaaat ggtggtcctc acctgtgaca cccctgaaga agatggtatc     180
acctggacct tggaccagag cagtgaggtc ttaggctctg gcaaaaccct gaccatccaa     240
gtcaaagagt ttggagatgc tggccagtac acctgtcaca aaggaggcga ggttctaagc     300
cattcgctcc tgctgcttca caaaaggaa gatggaattt ggtccactga tattttaaag     360
gaccagaaag aacccaaaaa taagacccttt ctaagatgcg aggccaagaa ttattctgga     420
cgtttcacct gctggtggct gacgacaatc agtactgatt tgacattcag tgtcaaaagc     480
agcagaggct cttctgaccc ccaagggggtg acgtgcggag ctgctacact ctctgcagag     540
agagtcagag gggacaacaa ggagtatgag tactcagtgg agtgccagga ggacagtgcc     600
tgcccagctg ctgaggagag tctgcccatt gaggtcatgg tggatgccgt tcacaagctc     660
aagtatgaaa actacaccag cagcttcttc atcagggaca tcatcaaacc tgacccaccc     720
aagaacttgc agctgaagcc attaaagaat tctcggcagg tggaggtcag ctgggagtac     780
cctgacacct ggagtactcc acattcctac ttctccctga cattctgcgt tcaggtccag     840
ggcaagagca agagagaaaa gaaagataga gtcttcacgg acaagacctc agccacggtc     900
atctgccgca aaaatgccag cattagcgtg cgggcccagg accgctacta tagctcatct     960
tggagcgaat gggcatctgt gccctgcagt taggttctga tccagga                  1007

<210> SEQ ID NO 6
<211> LENGTH: 1448
<212> TYPE: DNA
<213> ORGANISM: Homo sapiens

<400> SEQUENCE: 6
gtgaccgagc ggcgcggacg gccgcctgcc ccctctgcca cctggggcgg tgcgggcccg      60
gagcccggag cccgggtagc gcgtagagcc ggcgcgatgc acgtgcgctc actgcgagct     120
gcggcgccgc acagcttcgt ggcgctctgg cacccctgt tcctgctgcg ctccgccctg     180
gccgacttca gcctggacaa cgaggtgcac tcgagcttca tccaccggcg cctccgcagc     240
caggagcggc gggagatgca gcgcgagatc ctctccattt gggcttgcc ccaccgcccg     300
cgcccgcacc tccagggcaa gcacaactcg gcacccatgt tcatgctgga cctgtacaac     360
gccatggcgg tggaggaggg cggcgggccc ggcggcagg gcttctccta cccctacaag     420
gccgtcttca gtacccaggg ccccccttctg gccagcctgc aagatagcca tttcctcacc     480
gacgccgaca tggtcatgag cttcgtcaac ctcgtggaac atgacaagga attcttccac     540
ccacgctacc accatcgaga gttccggttt gatctttcca agatcccaga aggggaagct     600
gtcacggcag ccgaattccg gatctacaag gactacatcc gggaacgctt cgacaatgag     660
acgttccgga tcagcgttta tcaggtgctc caggagcact gggcaggga atcggatctc     720
ttcctgctcg acagccgtac cctctgggcc tcggaggagg ctggctggt gtttgacatc     780
acagccacca gcaaccactg ggtggtcaat ccgcggcaca acctgggcct gcagctctcg     840
gtggagacgc tggatgggca gagcatcaac cccaagttgg cgggcctgat tgggcggcac     900
gggcccccaga acaagcagcc cttcatggtg gctttcttca aggccacgga ggtccacttc     960
cgcagcatcc ggtccacggg gagcaaacag cgcagccaga accgctccaa gacgcccaag    1020
aaccaggaag ccctgcggat ggccaacgtg gcagagaaca gcagcagcga ccagaggcag    1080
```

| | |
|---|---:|
| gcctgtaaga agcacgagct gtatgtcagc ttccgagacc tgggctggca ggactggatc | 1140 |
| atcgcgcctg aaggctacgc cgcctactac tgtgagggg agtgtgcctt ccctctgaac | 1200 |
| tcctacatga acgccaccaa ccacgccatc gtgcagacgc tggtccactt catcaacccg | 1260 |
| gaaacggtgc ccaagccctg ctgtgcgccc acgcagctca atgccatctc cgtcctctac | 1320 |
| ttcgatgaca gctccaacgt catcctgaag aaatacagaa acatggtggt ccgggcctgt | 1380 |
| ggctgccact agctcctccg agaattcaga ccctttgggg ccaagttttt ctggatcctc | 1440 |
| cattgctc | 1448 |

<210> SEQ ID NO 7
<211> LENGTH: 732
<212> TYPE: DNA
<213> ORGANISM: Artificial sequence
<220> FEATURE:
<223> OTHER INFORMATION: Description of Artificial Sequence: Synthetic
      construct

<400> SEQUENCE: 7

| | |
|---|---:|
| atggcacagg tgcagctggt gcagtctggg gcagaggtga aaaagcccgg ggagtctctg | 60 |
| aagatctcct gtaagggttc tggatacagc tttaccagct actggatcgg ctgggtgcgc | 120 |
| cagatgcccg ggaaaggcct ggagtggatg gggatcatct atcctggtga ctctgatacc | 180 |
| agatacagcc cgtccttcca aggccaggtc accatctcag ccgacaagtc catcagcacc | 240 |
| gcctacctgc agtggagcag cctgaaggcc tcggacaccg ccatgtatta ctgtgcgaga | 300 |
| catgggtggg gtatggacgt ctggggccaa ggaaccctgg tcaccgtctc ctcaggtgga | 360 |
| ggcggttcag gcggaggtgg ctctggcggt ggcggatcgc aggctgtgct cactcagccg | 420 |
| tcctcagtgt ctggggcccc agggcagagg gtcaccatct cctgcactgg gagcagctcc | 480 |
| aacatcgggg caggttatga tgtacactgg taccagcagc ttccaggaac agcccccaaa | 540 |
| ctcctcatct atggtaacag caatcggccc tcaggggtcc ctgaccgatt ctctggctcc | 600 |
| aagtctggca cctcagcctc cctggccatc actgggctcc aggctgagga tgaggctgat | 660 |
| tattactgcc agtcctatga cagcagcctg agtggttcgg tattcggcgg agggaccaag | 720 |
| ctgaccgtcc ta | 732 |

<210> SEQ ID NO 8
<211> LENGTH: 979
<212> TYPE: DNA
<213> ORGANISM: Bos taurus

<400> SEQUENCE: 8

| | |
|---|---:|
| accctggatg ccatgaaggt tttctgcaac atggagactg cgagacctg cgtctacccc | 60 |
| aacccggcca gcgtccccaa gaagaactgg tggagcagca gagcaagga caagaaacac | 120 |
| atctggtttg agaaaccat caacggtggc ttccacttca gctatggaga tgacaacctg | 180 |
| gctcccaaca ccgccgacgt ccagatgacc ttcctgcgcc tgctgtccac cgagggctct | 240 |
| cagaacatca cctaccactg caagaacagc attgcctacc tggacgaagc tgctggcaac | 300 |
| ctcaagaagg ctctgctcat ccagggctcc aacgacgtgg agatccgggc tgagggcaac | 360 |
| agcaggttca catataccgt tctgaaggat ggctgcacga acacaccgg taagtggggc | 420 |
| aagactatga tcgagtaccg gtcacagaag acctcccgtc tgcccatcat tgacattgca | 480 |
| cccatggaca taggagggcc cgagcaggaa ttcgtgtgg acatagggcc tgtctgcttc | 540 |
| ttgtaaaaac ccgaacccag aaccaacaca atccattgca aacccaaagg acccaagaac | 600 |
| tttccaatcc cagtcactct aggactctgc actgaatggc tgacctgacc tgacgcccat | 660 |

|   |   |   |
|---|---|---|
| tcatcccacc ctctcacagt tcggactttg ctcccctctc taagagacct gaactgggca | 720 |
| gactgcaaaa tcaaatctcg gtgttctatt tatttattgt cttcctgtag gacctttggg | 780 |
| tcaaggcaga gacaggaaac taactggagt gagtcaaacg cccctgagt aactacccc | 840 |
| cggcccaagc aaggggcccc tgcaggtgcc gggcgcaggg actgcgcgcg tcctacacaa | 900 |
| cggcgctatt ctgtgtcaaa cacctctgta tttttaaaa cgtcaattga tattaaaaac | 960 |
| aaaaaaatta ttggaaagt | 979 |

<210> SEQ ID NO 9
<211> LENGTH: 662
<212> TYPE: DNA
<213> ORGANISM: Gallus gallus

<400> SEQUENCE: 9

|   |   |
|---|---|
| actgctcggc ccgacggacg gtgagagggc ctccgccgcc cgccatgcac ggccgccgcc | 60 |
| cgccccgctc cgccgctctc ctcctcctcc tcctccttct cacggccgcc gcagccgcgc | 120 |
| aggaccgcga cctcccggag gccgccgggg gctgcgtgca ggacgggcag agctacagcg | 180 |
| ataaggacgt gtggaagccg gagccgtgcc ggatctgcgt gtgcgacacc gggaccgttc | 240 |
| tgtgcgacga gatcatctgc gaggagccgc aggactgccc cagccccgaa atcccccttcg | 300 |
| gagagtgctg ccccgtctgc ccagcagagc tgcccgccgc cgcccgacaa cctgccccca | 360 |
| agggacagaa gggagaaccc ggagatatta agatgttgt aggaccccga gggcctccag | 420 |
| gaccacaggg cccagcagga gagcaggac agcgagggga ccgtggcgag aaggggggaga | 480 |
| agggtgctcc tggccccgt gggagggatg gagaacccgg caccctgga aacccaggcc | 540 |
| ccccggtcc ccccggacct cctggccccc ccggacttgg tggaaacttt gcggcgcaga | 600 |
| tggcgggcgg cttcgatgag aaggcgggtg gagggcagat gggtgtcatg cagggaccca | 660 |
| tg | 662 |

<210> SEQ ID NO 10
<211> LENGTH: 1944
<212> TYPE: DNA
<213> ORGANISM: Macaca mulatta

<400> SEQUENCE: 10

|   |   |
|---|---|
| agtttctggt ccccactttt ctcaacccca cagatgctcc ggggccctgc cccagctatg | 60 |
| gctcctgggg ctccctcatc cagccccagc cctatcctgg ctgtgctgct cttctcttct | 120 |
| ttggtgctgt cccccggccca ggccatcgtg gtttacaccg acaggaggt ccacggtgct | 180 |
| gtgggctccc gggtgaccct gcactgctcc ttctggtcca gtgagtgggt ctcagatgac | 240 |
| atctccttca cctggcgcta ccagcctgaa ggggcagag atgccatttc gatcttccac | 300 |
| tatgccaagg acaacccta cattgacgag gtggggacct tcaaagagcg catccagtgg | 360 |
| gtaggggacc ctcgctggaa ggatggctcc attgtcatac acaacctaga ctacagtgac | 420 |
| aatggcacgt tcacttgtga cgtcaaaaac cctccagaca tagtgggcaa gacctctcag | 480 |
| gtcacgctgt acgtctttga aaaagtgcca actaggtacg gggtggttct gggagctgtg | 540 |
| atcggggtg tcctcgggt ggtgctgttg ctgctgctgc ttttctacgt ggttcggtac | 600 |
| tgctggctac gcaggcaggc ggccctgcag aggaggctca gtgccatgga aaggggaaaa | 660 |
| ttgcacaagc cagcaaagga ctcgtcgaag cgcggcggc agacgccagt gctgtatgcc | 720 |
| atgctggacc acagcagaag caccaaagct gccagtgaga agaaggccaa ggggctgggg | 780 |
| gagtctcgca aggataagaa atagcggtta gcgggccggg cggggatcg ggggttaggg | 840 |

-continued

```
gtggagtccg ccaaaggcgc aaaggtggtg gtcatcgaga tggagctacg aaaggatgag      900
cagagctcgg agctccggcc tgctgtcaag tcccccagca gaaccagcct caaaaacgcc      960
ctcaagaaca tgatgggcct ggactcggac aagtgatcgc cacccccctac cccacgccct    1020 gccagagcag ggggacctag actcctctta ccccggtcta ggtgctttcc ctccttgctc    1080
ccccgccctg ccccgccctc acctcccttt gagatgtaag tttcattcca gaattcattc    1140
cccaggcaat tgtattctcc cccaccttca cccctggctt tctgggagcc caggagctaa    1200
tcctacccct cacctgcccc aggggctgtg tgtttggtgc ttgtccgcct gggcaccgag    1260
aagaaaggca ccttgatacc ctctgcctca agtccaggcc acctggcatt cccatctcct    1320
gcatccccca gcctgtcccc ctggctgttt cccttccctc ccttccctct actaggtggc    1380
ccagctccat actctgtccc ctccagctaa tacccagagc actcagatca gactctcctt    1440
cagggtttat ttaggttttt tttttttat tttttaatcc attctttgtt tgtttacctg    1500
tgctcatcct ctgcccttac acccatgact gaggaccaat gacgtcatgt ggcttttgca    1560
atttgtcacc cccacttaag tccttaatga agagccagcc caagcagagg ggcccctcat    1620
cctcacactt cggtatagca ttggtgcccc ctgaccactt tggagcactg ttctgggact    1680
ccaggtcttg aggaaagaga gagagagaga gagagagaga gaaaatggat cctcataggt    1740
cagggagtgg aggaggggga aaatgagcct taagaaatgg tttttaaaca accaaacaaa    1800
aagtaggaaa aacaaatggt tggggggag gaagaggctg cactccagcc acaggggatt    1860
cttaggattt ttctacattc tgtatatttc ttctcaaacc tccaaatgtc cttaaatgtt    1920
taataaacac tgacatttcc agaa                                            1944
```

<210> SEQ ID NO 11
<211> LENGTH: 1514
<212> TYPE: DNA
<213> ORGANISM: Macaca mulatta

<400> SEQUENCE: 11

```
ctagtaaaaa tgcatttta tagagatgtt gggaaaggct tgcttgaaat tacacgtggg       60
acttttacta gacaggcgct ttgaccagct aagcaacagg gctcccctcg tgtggggctt      120
ttagaatgta gcaaccactg acacacaggg aaggattatg ccgtcaggtg agaaggtggc      180
cgaccctgac tggctggaag cagacgcatt ctggtagctg attggtccac aggtggcgtg      240
aagcttgtca cgtcctcagg ctcccagcat tcaatcgtag cctttcagac agcttgaagc      300
cttctgtgga gagctcaaag ccttctgtgg agaactcaaa gctgtccgtg agccccaga      360 cgagccaaag cccaccttct cctcggcctg aactgtcttg aagatgagta acagtgggtt      420
tgggagctat ggcagcattt ctgctgctga tggagggagt ggaggcagtg accaactgtg      480
tgagagagat gcagctcctg ctattaagac ccaaagacct aaggtccgaa ttcaggacgt      540
tgtaccgtgt aatgtgaacc agcttctcag ctctactgtg tttgacactg tgttcaaggt      600 tagggaatt atagtttccc aggtctccat cgtggggta atcagagggg cagagaaggc      660
ttcaaatcac atttgttaca aaattgatga tatgactgcg aaaccaatcg aggcccgaca      720
gtggtttggt agagaaaaag tcaagcaagt gactccactg tcagtcggag catatgtcaa      780
agtgtttggt atcctcaaat gtcccacggg aacaaagacc cttgaggtat tgaaaattca      840
tgtcctagag gacatgaacg agttcactgt gcatattctg gaaacggtca atgcacacat      900
gatgctggat aaagcccgtc gtgataccac tgtagaaagt gtgcctgtgt tccatcgga      960 agtggatgat gctggggata acgatgagag tcaccgcagt ttcatccggg acgaagtgct   1020
```

-continued

```
gcgtttgatt catgagtgtc ctcaacagga agggaagagc atctatgagc tccaggctca   1080
gctctgcgac cttagcctca aggccatcaa ggaagcgatt gaatatctga cggtcgaggg   1140
ccacatctat cccactgtgg atcaggagca ttttaagtct gctgattgag cagggaaaa    1200 catcctttcc ttttcaaaag atccctgcat ccatctgaga gtaattttga cctgatgact   1260
ttttaggaag taggactaaa aaaaaaaaat ctcaagtggc attctttgtc aactcgctgc   1320
ttttctaact gctttgaact cttcagattt tctatatttg aagctcagag agagatggtg   1380
atggataaat tgacaactct gtaggattta ctagcaagct aatggaaaca tgatgacttg   1440
aggggaagaa aaactacaga aaatgtagaa atgtattatt taattgtgtt ggagcttctt   1500
ttcccaaaaa aaaa                                                    1514

<210> SEQ ID NO 12
<211> LENGTH: 1175
<212> TYPE: DNA
<213> ORGANISM: Macaca mulatta

<400> SEQUENCE: 12
ggttgacgtc cacacctaac gtccacatgg tcagcaccac cctgcctgtg gacagcagga     60
tgattgagga tgcaattcga agtcacagcg agtcagcctc accttcagcc ctgtccagta    120
gccccaacaa tctgagccca acaggctggt cacagccgga acacccgtg ccagcacaga     180 gagagcgggc accagtatcc gggacccagg cgaaaaacaa aattaggcct cgtggacaga    240
gagactcaag ctcttactgg gaaacagaag gcagtgaagt gatgccgtcc actcggactg    300
ggtcaggctc ttttggaact gtttataagg gcacatgcac ggagacgttg cagtaaagat    360
cctaaaggtt gtcaacccaa ccccagagca attccaggcc ttcaggaatg aggtggctgt    420
tctgcgcaaa acacggcgtg tgaacattct gcttttcatg gggtacgtga caaaggacaa    480
cctggcaatt gtgacccagt ggtgcgaggg cagcagcctc tacaaacacc tgtgtgtcca    540
ggagaccaag tttcagatgt tccagctaat ggacactgcc cggcagacgg ctcagggaat    600
ggactatttg catgcaaaga acatcatcca cagagacatg aaatccaaca atacatttcc    660
ccatgaaggc ctaacagtga aaactggaga ttttggtttg gcaacagtaa agtcacgctg    720
gggtggttct cagcaggttg aacaacctgc tggctctgtc ctgtggatgg tcccgggggt    780
gatccgaacg caggataaca acccattcag tttccagccg gatgtccact cctatggcat    840
cgtgtcgtat gagctgatga cgggggagct tcctcactct cacaccaaca actgagatca    900
gatcatcttc gtggtgggcc gagggatgcc tcccccgatc ttagtaagct acgtaagaac    960
tgccccaaag cgatgacgag gctggtcact gactgtgtga agaaagtaaa ggaagagagg   1020 cctctttttcc ccagatcctg tcttccattg agctgctcca acactctctg ctgaagatca   1080
gccggagcgc ttccgagccg tccttgcatc gggcagccca cactgaggat atcaatgcct   1140
gcacgctgac cacgtccccg ggcagcccac actga                             1175

<210> SEQ ID NO 13
<211> LENGTH: 1574
<212> TYPE: DNA
<213> ORGANISM: Macaca mulatta

<400> SEQUENCE: 13
atgtccgcag cctggatccc ggctctcagc cttggtgtgt gtctgctgct gctgccgggg     60
cccgcgggca gcgagggagc cgctcccatt gctatcacgt gttttaccag aggcttggac    120
atcaggaaag agaaagctga tgtcctctgc ccaggggct  gccctcttga ggaattctct    180
```

-continued

| | |
|---|---|
| gtgtatggga acatagtata tgcttctgta tcgagcatat gtggggctgc tgtccacagg | 240 |
| ggagtaatca gcaactcagg gggacctgta cgagtctaca gcctacctgg ccgagaaaac | 300 |
| tattcctcag tagatgccaa tggcatccag tctcaaatgc tttctagatg gtctgcttct | 360 |
| ttcacagtaa ctaaaggcaa aagtagtaca caggaggcca caggacaagc tgtgtccaca | 420 |
| gcacatccac caacaggtaa acgactaaag aaaacacctg agaagaaaac tggcaataaa | 480 |
| gattgtaaag cagacattgc atttctgatt gatggaagct ttaacattgg gcagcgccga | 540 |
| tttaatttac agaagaattt tgttggaaaa gtagctctaa tgttgggaat ggaacagaa | 600 |
| ggaccacatg tgggtcttgt tcaagccagt gaacatccca aaatagaatt ttacttgaaa | 660 |
| aactttacat cagccaaaga tgttttgttt gccataaagg aagtaggttt cagaggggt | 720 |
| aattccaata caggaaaagc cttgaagcat actgctcaga aattcttcac agtagatgct | 780 |
| ggagtaagaa aagggatccc caaagtggtg gtggtattta ttgatggttg gccttctgat | 840 |
| gacatcgagg aagcaggcat tgtggccaga gagtttggtg tcaatgtatt tatagtttct | 900 |
| gtggccaagc ctattcctga agaactggga atggttcagg atgttacatt tgttgacaag | 960 |
| gctgtctgtc ggaataatgg cttcttctct taccacatgc ccaactggtt tggcaccaca | 1020 |
| aaatacgtaa agcctctggt acagaagctg tgcactcatg aacaaatgat gtgcagcaag | 1080 |
| acctgttata actcagtgaa cattgccttt ctaattgatg ctccagcag tgttggagat | 1140 |
| agcaatttcc gcctcatgct tgaatttgtt tccaacatag ccaagacctt tgaaatctcg | 1200 |
| gacattggtg ccaagatagc tgctgtacag tttacttatg atcagcgcac ggagttcagt | 1260 |
| ttcactgact atagcaccaa agaggatgtc ctagctgtta tcagaaacat ccgctatatg | 1320 |
| agtggtggaa cagctactgg tgatgccatt tcctttactg ttagaaatgt gtttggccct | 1380 |
| ataagggaga gccccaacaa gaacttccta gtaattgtca cagatgggca gtcctatgat | 1440 |
| gatgtccaag gccctgcagc tgctgcacat gacgcaggta aggtccttgt tctttatagg | 1500 |
| agaagggaac agaaaaaaac agttcagtga attttaggag taaataaaaa tttaagcatt | 1560 |
| tcattgaaca aaca | 1574 |

<210> SEQ ID NO 14
<211> LENGTH: 2526
<212> TYPE: DNA
<213> ORGANISM: Drosophila melanogaster

<400> SEQUENCE: 14

| | |
|---|---|
| cgttgtgtct tgtgcgttgt gcggtgaagt tgcgccttcg ttctgaaacc taataagctg | 60 |
| agaatcagaa cctctggaca tctgaacgtc tgaaaatcca gcagcagcta ctcggaccgt | 120 |
| gcggtgcatc cttctccaga ctgagactaa gatccgattc cagccttagc cttcgacccc | 180 |
| acaaatcgcc gctttcaaga tgagagaaat cgtgaacctg caggccggcc agtgcggcaa | 240 |
| ccaaatcggc gctaagttct gggagatcat ttccgaggag cacggcatcg acagcaatgg | 300 |
| catctacgtg ggcgacagtg atctgcagct ggagcgcgtc agtgtctact acaacgaagc | 360 |
| atcggcagtc acgcggtcgt cgggtggtaa gtacgtgccc agggccatcc tgctcgatct | 420 |
| ggagcccgga accatggagt cggtgcgttc cggtccgtac ggacaactct tccggccgga | 480 |
| caacttcgtg tacggacagt cgggagcggg caacaactgg gccaagggtc actacaccga | 540 |
| gggcgccgag ctggtggaca atgtcctgga cgtggtccgc aaggagtgcg agaactgcga | 600 |
| ctgcctgcag ggcttccaat tgacgcactc gctgggcggc ggcactgggt ccggaatggg | 660 |
| caccctgctg atctcgaaga tccgcgagga gtaccccgac cgcatcatga acacctactc | 720 |

```
ggtggtgcca tcgcccaagg tgtcggacac cgtggtggag ccctacaacg ccaccctgtc      780
gatccaccag ctggtggaga acacagacga gacgtactgc atcgacaacg aggcgctgta      840
cgacatctgc ttccggacgc tgaaggtgtc gaatcccagc tacggagact gaaccacct      900
ggtctcgctg accatgtccg gggtgaccac ctgcctgcgt ttccccggcc agctgaacgc      960
cgatctgcgc aagctggcgg tcaacatggt tccattcccg cgtctccact tcttcatgcc     1020
cggattcgcg ccgctcacct cgcgcggatc gcagcagtac cgcgccctca ccgttcccga     1080
actgacccag cagatgttcg acgccaagaa catgatggcc gcctgtgatc cacgccacgg     1140
tcgctacctc acggtggccg ccgtcttccg cggccgcatg tccatgaagg aggtggacga     1200
gcagatgctg gcggtgcaga acaagaacag ctcctacttc gtggagtgga tcccgaacaa     1260
tgtgaagacc gcgtgtgcg acatcccgcc gaagggcctg aagatgtcct caacgttcat     1320
cggcaacacc acggccatcc aggagctgtt caagcggatc tccgagcagt tctcggccat     1380
gttccggcgc aaggccttcc tgcactggta caccggcgag gcatggacg agatggagtt     1440
caccgaggcg gagagcaaca tgaacgacct ggtgtccgag taccagcagt accaggaggc     1500
caccgccgac gacgagttcg acccggaggt caatcaggag gaggtcgagg gcgattgtat     1560
ttaatggtgt ggccagagga atgaggggcg tgcgtgacgg caggggggat agggatgtcc     1620
gctttctgcg cggcatgcgc caccagctgg cggccaagca ctgcagcatc ctgtgacccc     1680
cgccgttgga cacacacaca gtcacagcag acgcagacca cacaccacca caatcatcac     1740
acacggacag gaaggacatg cagacgaaca ggaaggtcaa gcgtagttag aacatcaaac     1800
ggaaatgttc ccaagcccat gcttccgcta ctccccatca tccagctcat ccatcgtcat     1860
ccatcatcgc ccatcccgcc gcatcatctc acatctcaca tctgacatct cgcatcttca     1920
tcttttgtt catttcggc acttgtcacc tcctctgcgc tatatacttt atactatact     1980
atactatata ccatatacac actttacacg gaggcacgtc tatcgcattt ctcgcagcca     2040
ttttcacccg ctttccaacc cacccaccac cacccatgtc actccattca taaccccaag     2100
ttatcccacg tcattcttat actactattt atatcgcaac gtcagcagaa ggaccacaag     2160
tatctagtat tgcaaaggat atcgaattta tgcagaaatc tcaaaacgag aatgtccagc     2220
gtctaggaag tcggcactca agacttggcg gcacttacgt ttagggctat actataaacg     2280
agctcatcca aagataatcg aacgacaact ctcatgagat cctctataaa aggcaatttc     2340
tgaaaagcat ctgcaattgt atttacataa tcttagggca caatctattc actttgtatt     2400
cgtgtgcagt acttctcttg tagttttata tggataaaaa catttgtacc caataaataa     2460
ctaataataa tggcaaacat ttttgacaaa taataaatgg aatttattta aaatttaaaa     2520
aaaaaa                                                                2526

<210> SEQ ID NO 15
<211> LENGTH: 843
<212> TYPE: DNA
<213> ORGANISM: Bos taurus

<400> SEQUENCE: 15
atgggtcctc gtggcctgcc tggtgaaaga ggacggactg ccctgccgg cgctgcaggt       60
gctcgaggca atgacggtca gccaggccct gcagggcctc cgggtcctgt gggtcctgct      120
ggcggtcctg gctttcctgg tgctcctggt gccaagggtg aagctggccc caccggtgct      180
cgaggtcccg aaggcgccca gggtcctcgc ggtgaaccgg gtactcctgg gtcccctggg      240
ccagctggtg ctgctggcaa ccctggaact gatggaatcc ctggagccaa gggatctgct      300
```

```
ggtgcccctg gcattgctgg tgctcccggc ttccctggac cccgtggtcc acccggccct    360
caaggtgcaa ctggtcctct gggcccaaaa ggtcaaacgg gtgagcctgg tattgctggc    420
ttcaaaggcg aacaaggccc aagggagaa ccgggcccta ctggtcccca aggagcccct    480
ggtcctgctg gtgaagaagg gaaaagaggt gccgtggag aacctggtgg tgctgggccc    540
gccggtcccc ctggagaaag aggcgctcct ggaaaccgtg gtttctcagg tcaggatggt    600
ctggcaggtc caagggagc ccctggagag cgaggaccca gtggcctcgc tggtcccaaa    660
ggcgccaacg gtgaccctgg ccgtcccgga gagcctggcc ttcctggagc ccggggtctc    720
actggtcgcc ctggtgatgc tggtcctcaa ggcaaagttg gtccttccgg agcccctggt    780
gaagacggtc gccctggacc cccaggtcct caggggggctc gtgggcagcc tggtgtcatg    840
tag                                                                  843
```

<210> SEQ ID NO 16
<211> LENGTH: 153
<212> TYPE: PRT
<213> ORGANISM: Homo sapiens

<400> SEQUENCE: 16

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

<210> SEQ ID NO 17
<211> LENGTH: 134
<212> TYPE: PRT
<213> ORGANISM: Homo sapiens

<400> SEQUENCE: 17

```
Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80
```

Gly Gly Thr Val Glu Arg Leu Phe Lys Asn Leu Ser Leu Ile Lys Lys
            85                  90                  95

Tyr Ile Asp Gly Gln Lys Lys Cys Gly Glu Glu Arg Arg Val
            100                 105                 110

Asn Gln Phe Leu Asp Tyr Leu Gln Glu Phe Leu Gly Val Met Asn Thr
            115                 120                 125

Glu Trp Ile Ile Glu Ser
        130

<210> SEQ ID NO 18
<211> LENGTH: 178
<212> TYPE: PRT
<213> ORGANISM: Homo sapiens

<400> SEQUENCE: 18

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 19
<211> LENGTH: 146
<212> TYPE: PRT
<213> ORGANISM: Homo sapiens

<400> SEQUENCE: 19

Met His Pro Leu Leu Asn Pro Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Ser Thr Ala Leu Arg Glu Leu Ile Glu
        35                  40                  45

Glu Leu Val Asn Ile Thr Gln Asn Gln Lys Ala Pro Leu Cys Asn Gly
50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

```
Gln Arg Met Leu Ser Gly Phe Cys Pro His Lys Val Ser Ala Gly Gln
                100                 105                 110

Phe Ser Ser Leu His Val Arg Asp Thr Lys Ile Glu Val Ala Gln Phe
            115                 120                 125

Val Lys Asp Leu Leu Leu His Leu Lys Lys Leu Phe Arg Glu Gly Gln
130                 135                 140

Phe Asn
145

<210> SEQ ID NO 20
<211> LENGTH: 328
<212> TYPE: PRT
<213> ORGANISM: Homo sapiens

<400> SEQUENCE: 20

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
290                 295                 300
```

```
Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 21
<211> LENGTH: 431
<212> TYPE: PRT
<213> ORGANISM: Homo sapiens

<400> SEQUENCE: 21

Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350
```

```
Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430

<210> SEQ ID NO 22
<211> LENGTH: 244
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 22

Met Ala Gln Val Gln Leu Val Gln Ser Gly Ala Glu Val Lys Lys Pro
1               5                   10                  15

Gly Glu Ser Leu Lys Ile Ser Cys Lys Gly Ser Gly Tyr Ser Phe Thr
            20                  25                  30

Ser Tyr Trp Ile Gly Trp Val Arg Gln Met Pro Gly Lys Gly Leu Glu
        35                  40                  45

Trp Met Gly Ile Ile Tyr Pro Gly Asp Ser Asp Thr Arg Tyr Ser Pro
    50                  55                  60

Ser Phe Gln Gly Gln Val Thr Ile Ser Ala Asp Lys Ser Ile Ser Thr
65                  70                  75                  80

Ala Tyr Leu Gln Trp Ser Ser Leu Lys Ala Ser Asp Thr Ala Met Tyr
                85                  90                  95

Tyr Cys Ala Arg His Gly Trp Gly Met Asp Val Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Gln Ala Val Leu Thr Gln Pro Ser Ser Val Ser
    130                 135                 140

Gly Ala Pro Gly Gln Arg Val Thr Ile Ser Cys Thr Gly Ser Ser Ser
145                 150                 155                 160

Asn Ile Gly Ala Gly Tyr Asp Val His Trp Tyr Gln Gln Leu Pro Gly
                165                 170                 175

Thr Ala Pro Lys Leu Leu Ile Tyr Gly Asn Ser Asn Arg Pro Ser Gly
            180                 185                 190

Val Pro Asp Arg Phe Ser Gly Ser Lys Ser Gly Thr Ser Ala Ser Leu
        195                 200                 205

Ala Ile Thr Gly Leu Gln Ala Glu Asp Glu Ala Asp Tyr Tyr Cys Gln
    210                 215                 220

Ser Tyr Asp Ser Ser Leu Ser Gly Ser Val Phe Gly Gly Gly Thr Lys
225                 230                 235                 240

Leu Thr Val Leu

<210> SEQ ID NO 23
<211> LENGTH: 181
<212> TYPE: PRT
<213> ORGANISM: Bos taurus
```

<400> SEQUENCE: 23

```
Thr Leu Asp Ala Met Lys Val Phe Cys Asn Met Glu Thr Gly Glu Thr
1               5                   10                  15

Cys Val Tyr Pro Asn Pro Ala Ser Val Pro Lys Lys Asn Trp Trp Ser
            20                  25                  30

Ser Lys Ser Lys Asp Lys Lys His Ile Trp Phe Gly Glu Thr Ile Asn
        35                  40                  45

Gly Gly Phe His Phe Ser Tyr Gly Asp Asp Asn Leu Ala Pro Asn Thr
    50                  55                  60

Ala Asp Val Gln Met Thr Phe Leu Arg Leu Leu Ser Thr Glu Gly Ser
65                  70                  75                  80

Gln Asn Ile Thr Tyr His Cys Lys Asn Ser Ile Ala Tyr Leu Asp Glu
                85                  90                  95

Ala Ala Gly Asn Leu Lys Lys Ala Leu Leu Ile Gln Gly Ser Asn Asp
            100                 105                 110

Val Glu Ile Arg Ala Glu Gly Asn Ser Arg Phe Thr Tyr Thr Val Leu
        115                 120                 125

Lys Asp Gly Cys Thr Lys His Thr Gly Lys Trp Gly Lys Thr Met Ile
130                 135                 140

Glu Tyr Arg Ser Gln Lys Thr Ser Arg Leu Pro Ile Ile Asp Ile Ala
145                 150                 155                 160

Pro Met Asp Ile Gly Gly Pro Glu Gln Glu Phe Gly Val Asp Ile Gly
                165                 170                 175

Pro Val Cys Phe Leu
            180
```

<210> SEQ ID NO 24
<211> LENGTH: 206
<212> TYPE: PRT
<213> ORGANISM: Gallus gallus

<400> SEQUENCE: 24

```
Met His Gly Arg Arg Pro Pro Arg Ser Ala Ala Leu Leu Leu Leu Leu
1               5                   10                  15

Leu Leu Leu Thr Ala Ala Ala Ala Gln Asp Arg Asp Leu Pro Glu
            20                  25                  30

Ala Ala Gly Gly Cys Val Gln Asp Gly Gln Ser Tyr Ser Asp Lys Asp
        35                  40                  45

Val Trp Lys Pro Glu Pro Cys Arg Ile Cys Val Cys Asp Thr Gly Thr
    50                  55                  60

Val Leu Cys Asp Glu Ile Ile Cys Glu Glu Pro Gln Asp Cys Pro Ser
65                  70                  75                  80

Pro Glu Ile Pro Phe Gly Glu Cys Cys Pro Val Cys Pro Ala Glu Leu
                85                  90                  95

Pro Ala Ala Ala Arg Gln Pro Gly Pro Lys Gly Gln Lys Gly Glu Pro
            100                 105                 110

Gly Asp Ile Lys Asp Val Val Gly Pro Arg Gly Pro Pro Gly Pro Gln
        115                 120                 125

Gly Pro Ala Gly Glu Gln Gly Gln Arg Gly Asp Arg Gly Glu Lys Gly
    130                 135                 140

Glu Lys Gly Ala Pro Gly Pro Arg Gly Arg Asp Gly Glu Pro Gly Thr
145                 150                 155                 160

Pro Gly Asn Pro Gly Pro Pro Gly Pro Pro Gly Pro Pro Gly Pro Pro
                165                 170                 175
```

```
Gly Leu Gly Gly Asn Phe Ala Ala Gln Met Ala Gly Gly Phe Asp Glu
            180                 185                 190
Lys Ala Gly Gly Gly Gln Met Gly Val Met Gln Gly Pro Met
        195                 200                 205
```

<210> SEQ ID NO 25
<211> LENGTH: 256
<212> TYPE: PRT
<213> ORGANISM: Macaca mulatta

<400> SEQUENCE: 25

```
Met Leu Arg Gly Pro Ala Pro Ala Met Ala Pro Gly Ala Pro Ser Ser
1               5                   10                  15
Ser Pro Ser Pro Ile Leu Ala Val Leu Leu Phe Ser Ser Leu Val Leu
            20                  25                  30
Ser Pro Ala Gln Ala Ile Val Val Tyr Thr Asp Arg Glu Val His Gly
        35                  40                  45
Ala Val Gly Ser Arg Val Thr Leu His Cys Ser Phe Trp Ser Ser Glu
    50                  55                  60
Trp Val Ser Asp Asp Ile Ser Phe Thr Trp Arg Tyr Gln Pro Glu Gly
65                  70                  75                  80
Gly Arg Asp Ala Ile Ser Ile Phe His Tyr Ala Lys Gly Gln Pro Tyr
                85                  90                  95
Ile Asp Glu Val Gly Thr Phe Lys Glu Arg Ile Gln Trp Val Gly Asp
            100                 105                 110
Pro Arg Trp Lys Asp Gly Ser Ile Val Ile His Asn Leu Asp Tyr Ser
        115                 120                 125
Asp Asn Gly Thr Phe Thr Cys Asp Val Lys Asn Pro Pro Asp Ile Val
    130                 135                 140
Gly Lys Thr Ser Gln Val Thr Leu Tyr Val Phe Glu Lys Val Pro Thr
145                 150                 155                 160
Arg Tyr Gly Val Val Leu Gly Ala Val Ile Gly Gly Val Leu Gly Val
                165                 170                 175
Val Leu Leu Leu Leu Leu Leu Phe Tyr Val Val Arg Tyr Cys Trp Leu
            180                 185                 190
Arg Arg Gln Ala Ala Leu Gln Arg Arg Leu Ser Ala Met Glu Lys Gly
        195                 200                 205
Lys Leu His Lys Pro Ala Lys Asp Ser Ser Lys Arg Gly Arg Gln Thr
    210                 215                 220
Pro Val Leu Tyr Ala Met Leu Asp His Ser Arg Ser Thr Lys Ala Ala
225                 230                 235                 240
Ser Glu Lys Lys Ala Lys Gly Leu Gly Glu Ser Arg Lys Asp Lys Lys
                245                 250                 255
```

<210> SEQ ID NO 26
<211> LENGTH: 262
<212> TYPE: PRT
<213> ORGANISM: Macaca mulatta

<400> SEQUENCE: 26

```
Met Ser Asn Ser Gly Phe Gly Tyr Gly Ser Ile Ser Ala Ala Asp
1               5                   10                  15
Gly Gly Ser Gly Gly Ser Asp Gln Leu Cys Glu Arg Asp Ala Ala Pro
            20                  25                  30
Ala Ile Lys Thr Gln Arg Pro Lys Val Arg Ile Gln Asp Val Val Pro
        35                  40                  45
```

```
Cys Asn Val Asn Gln Leu Leu Ser Ser Thr Val Phe Asp Thr Val Phe
         50                  55                  60

Lys Val Arg Gly Ile Ile Val Ser Gln Val Ser Ile Val Gly Val Ile
 65                  70                  75                  80

Arg Gly Ala Glu Lys Ala Ser Asn His Ile Cys Tyr Lys Ile Asp Asp
                 85                  90                  95

Met Thr Ala Lys Pro Ile Glu Ala Arg Gln Trp Phe Gly Arg Glu Lys
            100                 105                 110

Val Lys Gln Val Thr Pro Leu Ser Val Gly Ala Tyr Val Lys Val Phe
        115                 120                 125

Gly Ile Leu Lys Cys Pro Thr Gly Thr Lys Thr Leu Glu Val Leu Lys
130                 135                 140

Ile His Val Leu Glu Asp Met Asn Glu Phe Thr Val His Ile Leu Glu
145                 150                 155                 160

Thr Val Asn Ala His Met Met Leu Asp Lys Ala Arg Arg Asp Thr Thr
                165                 170                 175

Val Glu Ser Val Pro Val Phe Pro Ser Glu Val Asp Asp Ala Gly Asp
            180                 185                 190

Asn Asp Glu Ser His Arg Ser Phe Ile Arg Asp Glu Val Leu Arg Leu
        195                 200                 205

Ile His Glu Cys Pro Gln Gln Glu Gly Lys Ser Ile Tyr Glu Leu Gln
    210                 215                 220

Ala Gln Leu Cys Asp Leu Ser Leu Lys Ala Ile Lys Glu Ala Ile Glu
225                 230                 235                 240

Tyr Leu Thr Val Glu Gly His Ile Tyr Pro Thr Val Asp Gln Glu His
                245                 250                 255

Phe Lys Ser Ala Asp Ser
            260

<210> SEQ ID NO 27
<211> LENGTH: 509
<212> TYPE: PRT
<213> ORGANISM: Macaca mulatta

<400> SEQUENCE: 27

Met Ser Ala Ala Trp Ile Pro Ala Leu Ser Leu Gly Val Cys Leu Leu
 1               5                  10                  15

Leu Leu Pro Gly Pro Ala Gly Ser Glu Gly Ala Ala Pro Ile Ala Ile
                 20                  25                  30

Thr Cys Phe Thr Arg Gly Leu Asp Ile Arg Lys Glu Lys Ala Asp Val
             35                  40                  45

Leu Cys Pro Gly Gly Cys Pro Leu Glu Glu Phe Ser Val Tyr Gly Asn
 50                  55                  60

Ile Val Tyr Ala Ser Val Ser Ser Ile Cys Gly Ala Ala Val His Arg
 65                  70                  75                  80

Gly Val Ile Ser Asn Ser Gly Pro Val Arg Val Tyr Ser Leu Pro
                 85                  90                  95

Gly Arg Glu Asn Tyr Ser Ser Val Asp Ala Asn Gly Ile Gln Ser Gln
            100                 105                 110

Met Leu Ser Arg Trp Ser Ala Ser Phe Thr Val Thr Lys Gly Lys Ser
        115                 120                 125

Ser Thr Gln Glu Ala Thr Gly Gln Ala Val Ser Thr Ala His Pro Pro
130                 135                 140

Thr Gly Lys Arg Leu Lys Lys Thr Pro Glu Lys Lys Thr Gly Asn Lys
145                 150                 155                 160
```

-continued

```
Asp Cys Lys Ala Asp Ile Ala Phe Leu Ile Asp Gly Ser Phe Asn Ile
                165                 170                 175

Gly Gln Arg Arg Phe Asn Leu Gln Lys Asn Phe Val Gly Lys Val Ala
            180                 185                 190

Leu Met Leu Gly Ile Gly Thr Glu Gly Pro His Val Gly Leu Val Gln
        195                 200                 205

Ala Ser Glu His Pro Lys Ile Glu Phe Tyr Leu Lys Asn Phe Thr Ser
    210                 215                 220

Ala Lys Asp Val Leu Phe Ala Ile Lys Glu Val Gly Phe Arg Gly Gly
225                 230                 235                 240

Asn Ser Asn Thr Gly Lys Ala Leu Lys His Thr Ala Gln Lys Phe Phe
                245                 250                 255

Thr Val Asp Ala Gly Val Arg Lys Gly Ile Pro Lys Val Val Val Val
            260                 265                 270

Phe Ile Asp Gly Trp Pro Ser Asp Ile Glu Glu Ala Gly Ile Val
        275                 280                 285

Ala Arg Glu Phe Gly Val Asn Val Phe Ile Val Ser Val Ala Lys Pro
    290                 295                 300

Ile Pro Glu Glu Leu Gly Met Val Gln Asp Val Thr Phe Val Asp Lys
305                 310                 315                 320

Ala Val Cys Arg Asn Asn Gly Phe Phe Ser Tyr His Met Pro Asn Trp
                325                 330                 335

Phe Gly Thr Thr Lys Tyr Val Lys Pro Leu Val Gln Lys Leu Cys Thr
            340                 345                 350

His Glu Gln Met Met Cys Ser Lys Thr Cys Tyr Asn Ser Val Asn Ile
        355                 360                 365

Ala Phe Leu Ile Asp Gly Ser Ser Val Gly Asp Ser Asn Phe Arg
    370                 375                 380

Leu Met Leu Glu Phe Val Ser Asn Ile Ala Lys Thr Phe Glu Ile Ser
385                 390                 395                 400

Asp Ile Gly Ala Lys Ile Ala Ala Val Gln Phe Thr Tyr Asp Gln Arg
                405                 410                 415

Thr Glu Phe Ser Phe Thr Asp Tyr Ser Thr Lys Glu Asp Val Leu Ala
            420                 425                 430

Val Ile Arg Asn Ile Arg Tyr Met Ser Gly Gly Thr Ala Thr Gly Asp
        435                 440                 445

Ala Ile Ser Phe Thr Val Arg Asn Val Phe Gly Pro Ile Arg Glu Ser
    450                 455                 460

Pro Asn Lys Asn Phe Leu Val Ile Val Thr Asp Gly Gln Ser Tyr Asp
465                 470                 475                 480

Asp Val Gln Gly Pro Ala Ala Ala His Asp Ala Gly Lys Val Leu
                485                 490                 495

Val Leu Tyr Arg Arg Arg Glu Gln Lys Lys Thr Val Gln
            500                 505

<210> SEQ ID NO 28
<211> LENGTH: 454
<212> TYPE: PRT
<213> ORGANISM: Drosophila melanogaster

<400> SEQUENCE: 28

Met Arg Glu Ile Val Asn Leu Gln Ala Gly Gln Cys Gly Asn Gln Ile
1               5                   10                  15

Gly Ala Lys Phe Trp Glu Ile Ile Ser Glu Glu His Gly Ile Asp Ser
            20                  25                  30
```

```
Asn Gly Ile Tyr Val Gly Asp Ser Asp Leu Gln Leu Glu Arg Val Ser
     35                  40                  45
Val Tyr Tyr Asn Glu Ala Ser Ala Val Thr Arg Ser Ser Gly Gly Lys
 50                  55                  60
Tyr Val Pro Arg Ala Ile Leu Leu Asp Leu Glu Pro Gly Thr Met Glu
 65                  70                  75                  80
Ser Val Arg Ser Gly Pro Tyr Gly Gln Leu Phe Arg Pro Asp Asn Phe
                 85                  90                  95
Val Tyr Gly Gln Ser Gly Ala Gly Asn Asn Trp Ala Lys Gly His Tyr
                100                 105                 110
Thr Glu Gly Ala Glu Leu Val Asp Asn Val Leu Asp Val Val Arg Lys
            115                 120                 125
Glu Cys Glu Asn Cys Asp Cys Leu Gln Gly Phe Gln Leu Thr His Ser
        130                 135                 140
Leu Gly Gly Gly Thr Gly Ser Gly Met Gly Thr Leu Leu Ile Ser Lys
145                 150                 155                 160
Ile Arg Glu Glu Tyr Pro Asp Arg Ile Met Asn Thr Tyr Ser Val Val
                165                 170                 175
Pro Ser Pro Lys Val Ser Asp Thr Val Val Glu Pro Tyr Asn Ala Thr
            180                 185                 190
Leu Ser Ile His Gln Leu Val Glu Asn Thr Asp Glu Thr Tyr Cys Ile
        195                 200                 205
Asp Asn Glu Ala Leu Tyr Asp Ile Cys Phe Arg Thr Leu Lys Val Ser
    210                 215                 220
Asn Pro Ser Tyr Gly Asp Leu Asn His Leu Val Ser Leu Thr Met Ser
225                 230                 235                 240
Gly Val Thr Thr Cys Leu Arg Phe Pro Gly Gln Leu Asn Ala Asp Leu
                245                 250                 255
Arg Lys Leu Ala Val Asn Met Val Pro Phe Pro Arg Leu His Phe Phe
            260                 265                 270
Met Pro Gly Phe Ala Pro Leu Thr Ser Arg Gly Ser Gln Gln Tyr Arg
        275                 280                 285
Ala Leu Thr Val Pro Glu Leu Thr Gln Gln Met Phe Asp Ala Lys Asn
    290                 295                 300
Met Met Ala Ala Cys Asp Pro Arg His Gly Arg Tyr Leu Thr Val Ala
305                 310                 315                 320
Ala Val Phe Arg Gly Arg Met Ser Met Lys Glu Val Asp Glu Gln Met
                325                 330                 335
Leu Ala Val Gln Asn Lys Asn Ser Ser Tyr Phe Val Glu Trp Ile Pro
            340                 345                 350
Asn Asn Val Lys Thr Ala Val Cys Asp Ile Pro Pro Lys Gly Leu Lys
        355                 360                 365
Met Ser Ser Thr Phe Ile Gly Asn Thr Thr Ala Ile Gln Glu Leu Phe
    370                 375                 380
Lys Arg Ile Ser Glu Gln Phe Ser Ala Met Phe Arg Arg Lys Ala Phe
385                 390                 395                 400
Leu His Trp Tyr Thr Gly Glu Gly Met Asp Glu Met Glu Phe Thr Glu
                405                 410                 415
Ala Glu Ser Asn Met Asn Asp Leu Val Ser Glu Tyr Gln Gln Tyr Gln
            420                 425                 430
Glu Ala Thr Ala Asp Asp Glu Phe Asp Pro Glu Val Asn Gln Glu Glu
        435                 440                 445
Val Glu Gly Asp Cys Ile
    450
```

```
<210> SEQ ID NO 29
<211> LENGTH: 280
<212> TYPE: PRT
<213> ORGANISM: Bos taurus

<400> SEQUENCE: 29

Met Gly Pro Arg Gly Leu Pro Gly Glu Arg Gly Arg Thr Gly Pro Ala
1               5                   10                  15

Gly Ala Ala Gly Ala Arg Gly Asn Asp Gly Gln Pro Gly Pro Ala Gly
            20                  25                  30

Pro Pro Gly Pro Val Gly Pro Ala Gly Gly Pro Gly Phe Pro Gly Ala
        35                  40                  45

Pro Gly Ala Lys Gly Glu Ala Gly Pro Thr Gly Ala Arg Gly Pro Glu
    50                  55                  60

Gly Ala Gln Gly Pro Arg Gly Glu Pro Gly Thr Pro Gly Ser Pro Gly
65                  70                  75                  80

Pro Ala Gly Ala Ala Gly Asn Pro Gly Thr Asp Gly Ile Pro Gly Ala
                85                  90                  95

Lys Gly Ser Ala Gly Ala Pro Gly Ile Ala Gly Ala Pro Gly Phe Pro
            100                 105                 110

Gly Pro Arg Gly Pro Pro Gly Pro Gln Gly Ala Thr Gly Pro Leu Gly
        115                 120                 125

Pro Lys Gly Gln Thr Gly Glu Pro Gly Ile Ala Gly Phe Lys Gly Glu
    130                 135                 140

Gln Gly Pro Lys Gly Glu Pro Gly Pro Thr Gly Pro Gln Gly Ala Pro
145                 150                 155                 160

Gly Pro Ala Gly Glu Glu Gly Lys Arg Gly Ala Arg Gly Glu Pro Gly
                165                 170                 175

Gly Ala Gly Pro Ala Gly Pro Pro Gly Glu Arg Gly Ala Pro Gly Asn
            180                 185                 190

Arg Gly Phe Ser Gly Gln Asp Gly Leu Ala Gly Pro Lys Gly Ala Pro
        195                 200                 205

Gly Glu Arg Gly Pro Ser Gly Leu Ala Gly Pro Lys Gly Ala Asn Gly
    210                 215                 220

Asp Pro Gly Arg Pro Gly Glu Pro Gly Leu Pro Gly Ala Arg Gly Leu
225                 230                 235                 240

Thr Gly Arg Pro Gly Asp Ala Gly Pro Gln Gly Lys Val Gly Pro Ser
                245                 250                 255

Gly Ala Pro Gly Glu Asp Gly Arg Pro Gly Pro Pro Gly Pro Gln Gly
            260                 265                 270

Ala Arg Gly Gln Pro Gly Val Met
        275                 280

<210> SEQ ID NO 30
<211> LENGTH: 897
<212> TYPE: DNA
<213> ORGANISM: Artificial Sequence
<220> FEATURE:
<223> OTHER INFORMATION: Description of Artificial Sequence: Synthetic
      construct
<220> FEATURE:
<221> NAME/KEY: CDS
<222> LOCATION: (1)..(876)
<220> FEATURE:
<221> NAME/KEY: CDS
<222> LOCATION: (880)..(897)
```

<400> SEQUENCE: 30

```
tac gac gat gac gat aag gat ccg agc tcg aga tct atg ggt cct cgt        48
Tyr Asp Asp Asp Asp Lys Asp Pro Ser Ser Arg Ser Met Gly Pro Arg
 1               5                  10                  15 ggc ctg cct ggt gaa aga gga cgg act ggc cct gcc ggc gct gca ggt        96
Gly Leu Pro Gly Glu Arg Gly Arg Thr Gly Pro Ala Gly Ala Ala Gly
             20                  25                  30 gct cga ggc aat gac ggt cag cca ggc cct gca ggg cct ccg ggt cct       144
Ala Arg Gly Asn Asp Gly Gln Pro Gly Pro Ala Gly Pro Pro Gly Pro
         35                  40                  45 gtg ggt cct gct ggc ggt cct ggc ttt cct ggt gct cct ggt gcc aag       192
Val Gly Pro Ala Gly Gly Pro Gly Phe Pro Gly Ala Pro Gly Ala Lys
     50                  55                  60 ggt gaa gct ggc ccc acc ggt gct cga ggt ccc gaa ggc gcc cag ggt       240
Gly Glu Ala Gly Pro Thr Gly Ala Arg Gly Pro Glu Gly Ala Gln Gly
 65                  70                  75                  80 cct cgc ggt gaa ccg ggt act cct ggg tcc cct ggg cca gct ggt gct       288
Pro Arg Gly Glu Pro Gly Thr Pro Gly Ser Pro Gly Pro Ala Gly Ala
                 85                  90                  95 gct ggc aac cct gga act gat gga atc cct gga gcc aag gga tct gct       336
Ala Gly Asn Pro Gly Thr Asp Gly Ile Pro Gly Ala Lys Gly Ser Ala
            100                 105                 110 ggt gcc cct ggc att gct ggt gct ccc ggc ttc cct gga ccc cgt ggt       384
Gly Ala Pro Gly Ile Ala Gly Ala Pro Gly Phe Pro Gly Pro Arg Gly
        115                 120                 125 cca ccc ggc cct caa ggt gca act ggt cct ctg ggc cca aaa ggt caa       432
Pro Pro Gly Pro Gln Gly Ala Thr Gly Pro Leu Gly Pro Lys Gly Gln
    130                 135                 140 acg ggt gag cct ggt att gct ggc ttc aaa ggc gaa caa ggc ccc aag       480
Thr Gly Glu Pro Gly Ile Ala Gly Phe Lys Gly Glu Gln Gly Pro Lys
145                 150                 155                 160 gga gaa ccg ggc cct act ggt ccc caa gga gcc cct ggt cct gct ggt       528
Gly Glu Pro Gly Pro Thr Gly Pro Gln Gly Ala Pro Gly Pro Ala Gly
                165                 170                 175 gaa gaa ggg aaa aga ggt gcc cgt gga gaa cct ggt ggt gct ggg ccc       576
Glu Glu Gly Lys Arg Gly Ala Arg Gly Glu Pro Gly Gly Ala Gly Pro
            180                 185                 190 gcc ggt ccc cct gga gaa aga ggc gct cct gga aac cgt ggt ttc tca       624
Ala Gly Pro Pro Gly Glu Arg Gly Ala Pro Gly Asn Arg Gly Phe Ser
        195                 200                 205 ggt cag gat ggt ctg gca ggt ccc aag gga gcc cct gga gag cga gga       672
Gly Gln Asp Gly Leu Ala Gly Pro Lys Gly Ala Pro Gly Glu Arg Gly
    210                 215                 220 ccc agt ggc ctc gct ggt ccc aaa ggc gcc aac ggt gac cct ggc cgt       720
Pro Ser Gly Leu Ala Gly Pro Lys Gly Ala Asn Gly Asp Pro Gly Arg
225                 230                 235                 240 ccc gga gag cct ggc ctt cct gga agc ccg ggt ctc act ggt cgc cct       768
Pro Gly Glu Pro Gly Leu Pro Gly Ser Pro Gly Leu Thr Gly Arg Pro
                245                 250                 255 ggt gat gct ggt cct caa ggc aaa gtt ggt cct tcc gga gcc cct ggt       816
Gly Asp Ala Gly Pro Gln Gly Lys Val Gly Pro Ser Gly Ala Pro Gly
            260                 265                 270 gaa gac ggt cgc cct gga ccc cca ggt cct cag ggg gct cgt ggg cag       864
Glu Asp Gly Arg Pro Gly Pro Pro Gly Pro Gln Gly Ala Arg Gly Gln
        275                 280                 285 cct ggt gtc atg tag aag ctt gtc gtt gga tgg                           897
Pro Gly Val Met     Lys Leu Val Val Gly Trp
    290                 295
```

```
<210> SEQ ID NO 31
<211> LENGTH: 292
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 31

Tyr Asp Asp Asp Asp Lys Asp Pro Ser Ser Arg Ser Met Gly Pro Arg
1               5                   10                  15

Gly Leu Pro Gly Glu Arg Gly Arg Thr Gly Pro Ala Gly Ala Ala Gly
            20                  25                  30

Ala Arg Gly Asn Asp Gly Gln Pro Gly Pro Ala Gly Pro Pro Gly Pro
        35                  40                  45

Val Gly Pro Ala Gly Gly Pro Gly Phe Pro Gly Ala Pro Gly Ala Lys
    50                  55                  60

Gly Glu Ala Gly Pro Thr Gly Ala Arg Gly Pro Glu Gly Ala Gln Gly
65                  70                  75                  80

Pro Arg Gly Glu Pro Gly Thr Pro Gly Ser Pro Gly Pro Ala Gly Ala
                85                  90                  95

Ala Gly Asn Pro Gly Thr Asp Gly Ile Pro Gly Ala Lys Gly Ser Ala
            100                 105                 110

Gly Ala Pro Gly Ile Ala Gly Ala Pro Gly Phe Pro Gly Pro Arg Gly
        115                 120                 125

Pro Pro Gly Pro Gln Gly Ala Thr Gly Pro Leu Gly Pro Lys Gly Gln
    130                 135                 140

Thr Gly Glu Pro Gly Ile Ala Gly Phe Lys Gly Glu Gln Gly Pro Lys
145                 150                 155                 160

Gly Glu Pro Gly Pro Thr Gly Pro Gln Gly Ala Pro Gly Pro Ala Gly
                165                 170                 175

Glu Glu Gly Lys Arg Gly Ala Arg Gly Glu Pro Gly Gly Ala Gly Pro
            180                 185                 190

Ala Gly Pro Pro Gly Glu Arg Gly Ala Pro Gly Asn Arg Gly Phe Ser
        195                 200                 205

Gly Gln Asp Gly Leu Ala Gly Pro Lys Gly Ala Pro Gly Glu Arg Gly
    210                 215                 220

Pro Ser Gly Leu Ala Gly Pro Lys Gly Ala Asn Gly Asp Pro Gly Arg
225                 230                 235                 240

Pro Gly Glu Pro Gly Leu Pro Gly Ser Pro Gly Leu Thr Gly Arg Pro
                245                 250                 255

Gly Asp Ala Gly Pro Gln Gly Lys Val Gly Pro Ser Gly Ala Pro Gly
            260                 265                 270

Glu Asp Gly Arg Pro Gly Pro Pro Gly Pro Gln Gly Ala Arg Gly Gln
        275                 280                 285

Pro Gly Val Met
    290

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      construct
```

-continued

```
<400> SEQUENCE: 32

Lys Leu Val Val Gly Trp
1               5
```